(12) United States Patent
Tanaka et al.

(10) Patent No.: US 10,683,341 B2
(45) Date of Patent: Jun. 16, 2020

(54) ALBUMIN-SUGAR CHAIN COMPLEX

(71) Applicants: Glytech, Inc., Kyoto (JP); RIKEN, Saitama (JP)

(72) Inventors: Katsunori Tanaka, Wako (JP); Yasuyoshi Watanabe, Wako (JP); Akihiro Ogura, Wako (JP); Takahiro Yamamoto, Kyoto (JP)

(73) Assignees: Glytech, Inc., Kyoto (JP); RIKEN, Saitama (JP)

( * ) Notice: Subject to any disclaimer, the term of this patent is extended or adjusted under 35 U.S.C. 154(b) by 76 days.

(21) Appl. No.: 15/740,511

(22) PCT Filed: Jun. 30, 2016

(86) PCT No.: PCT/JP2016/069438
§ 371 (c)(1),
(2) Date: Dec. 28, 2017

(87) PCT Pub. No.: WO2017/002918
PCT Pub. Date: Jan. 5, 2017

(65) Prior Publication Data
US 2018/0186859 A1  Jul. 5, 2018

(30) Foreign Application Priority Data

Jun. 30, 2015 (JP) ................. 2015-132002

(51) Int. Cl.
| | | |
|---|---|---|
| C07K 14/765 | (2006.01) | |
| A61K 31/702 | (2006.01) | |
| A61K 31/715 | (2006.01) | |
| A61K 47/54 | (2017.01) | |
| A61K 49/00 | (2006.01) | |
| A61K 47/64 | (2017.01) | |
| A61K 47/42 | (2017.01) | |

(52) U.S. Cl.
CPC .......... *C07K 14/765* (2013.01); *A61K 31/702* (2013.01); *A61K 31/715* (2013.01); *A61K 47/42* (2013.01); *A61K 47/549* (2017.08); *A61K 47/643* (2017.08); *A61K 49/0019* (2013.01); *A61K 49/0032* (2013.01); *A61K 49/0056* (2013.01)

(58) Field of Classification Search
None
See application file for complete search history.

(56) References Cited

U.S. PATENT DOCUMENTS

| | | |
|---|---|---|
| 2009/0099071 A1 | 4/2009 | Nakajou et al. |
| 2010/0008857 A1 | 1/2010 | Fukase et al. |

FOREIGN PATENT DOCUMENTS

| | | |
|---|---|---|
| JP | 2008-043285 A | 2/2008 |
| JP | 2015-030702 A | 2/2015 |
| WO | 2008/096760 A1 | 8/2008 |

OTHER PUBLICATIONS

Tanaka et al., "A combined 6π-azaelectrocyclization/Staudinger Approach to Protein and Cell Engineering: Noninvasive Tumor Targeting by N-Glycan-Engineered Lymphocytes", Journal of Carbohydrate Chemistry 29(3): 118-132 (2010) (Year: 2010).*
Extended European Search Report issued in European Application No. 16818026.3, dated Feb. 12, 2019 (11 pages).
H. J. Gabius et al: "Glycopeptide-albumin derivative: Its preparation and histochemical ligand properties", Histochemical Journal, vol. 23, No. 7, Jul. 1, 1991, pp. 303-311 (9 pages).
A. A. Gooley et al: "Characterization of a single glycosylated asparagine site on a glycopeptide using solid-phase Edman degradation", Glycoconjugate Journal, vol. 11, No. 3, Jun. 1, 1994, pp. 180-186 (7 pages).
Y. Sakamoto et al: "Structural study of the glycosylated and unglycosylated forms of a genetic variant of human serum albumin (63 Asp -> Asn)", Biochimica et Biophysica Acta, vol. 1252, No. 2, Oct. 1, 1995, pp. 209-216 (8 pages).
Y. Ohyama et al: "Frontal affinity chromatography of ovalbumin glycoasparagines on a concanavalin A-sepharose column. A quantitative study of the binding specificity of the lectin", Journal of Biological Chemistry, Jun. 10, 1985, pp. 6882-6887 (6 pages).
André, S. et al.; "Neoglycoproteins with the Synthetic Complex Biantennary Nonasaccharide or Its alpha2,3/alpha2,6-Sialylated Derivatives: Their Preparation, Assessment of Their Ligand Properties for Purified Lectins, for Tumor Cells in Vitro, and in Tissue Sections, and Their Biodistribution in Tumor-Bearing Mice"; Bioconjugate Chemistry, vol. 8, 1997, pp. 845-855 (11 pages).
Unverzagt, C. et al.; "Structure-Activity Profiles of Complex Biantennary Glycans with Core Fucosylation and with/without Additional alpha2,3/alpha2,6 Sialylation: Synthesis of Neoglycoproteins and Their Properties in Lectin Assays, Cell Binding, and Organ Uptake"; Journal of Medicinal Chemistry, vol. 45, 2002, pp. 478-491 (14 pages).
Ogura, A. et al.; "In vivo kinetics and biodistribution analysis of neoglycoproteins: effects of chemically introduced glycans on proteins"; Glycoconjugate Journal, vol. 31, 2014, pp. 273-279 (7 pages).

(Continued)

*Primary Examiner* — Anand U Desai
(74) *Attorney, Agent, or Firm* — Osha Liang LLP

(57) ABSTRACT

An object of the present invention is to provide an albumin-sugar chain complex bound with a number of sugar chains sufficient for obtaining a sugar chain clustering effect while also being able to exist comparatively stably in the body. The present invention provides an albumin-sugar chain complex having five or more molecules of an asparagine-linked sugar chain bound per molecule of albumin; a carrier for selectively delivering a functional molecule to a target tissue in the body that contains the aforementioned albumin-sugar chain complex; and a bioimaging probe having the aforementioned albumin-sugar chain complex as an active ingredient thereof that is administered into the body of an animal.

10 Claims, 7 Drawing Sheets

(56) References Cited

OTHER PUBLICATIONS

Tanaka, K. et al.; "Noninvasive Imaging of Dendrimer-Type N-Glycan Clusters: In Vivo Dynamics Dependence on Oligosaccharide Structure"; Angewandte Chemie International Edition, vol. 49, 2010, pp. 8195-8200 (6 pages).

Wang, H. et al.; "Design and synthesis of glycoprotein-based multivalent glyco-ligands for influenza hemagglutinin and human galectin-3"; Bioorganic & Medicinal Chemistry, vol. 21, Issue 7, 2013, ISSN 0968-0896, pp. 2037-2044 (8 pages).

Ogura, A. et al.; "Kagakuteki na Tosa no Donyu ni yoru Tanpakushitsu no Seitainai Dotai to Shuseki Seigyo"; 94th Annual Meeting of the Chemical Society of Japan in Spring (2014), Koen Yokoshu IV, 2014 (with English Abstract in first page), ISSN 0285-7626, p. 1457 (2H6-08) (3 pages).

Kobayashi, K. et al.; "Glycocluster materials"; Journal of the Agricultural Chemical Society of Japan, vol. 78, No. 9, 2004, ISSN 0002-1407, pp. 870-873 (4 pages).

Ogura, A. et al.; "Glycan multivalency effects toward albumin enable N-glycan-dependent tumor targeting"; Bioorganic & Medicinal Chemistry Letters, vol. 26, Issue 9, Mar. 2016, ISSN 0960-894X, pp. 2251-2254 (4 pages).

Ogura, A. et al.; "Visualizing Trimming Dependence of Biodistribution and Kinetics with Homo- and Heterogeneous N-Glycoclusters of Fluorescent Albumin"; Scientific Reports, vol. 6, 21797, Feb. 2016, ISSN 2045-2322, pp. 1-10 (10 pages).

International Search Report of the International Searching Authority issued in PCT/JP2016/069438 dated Sep. 27, 2016 (5 pages)

\* cited by examiner

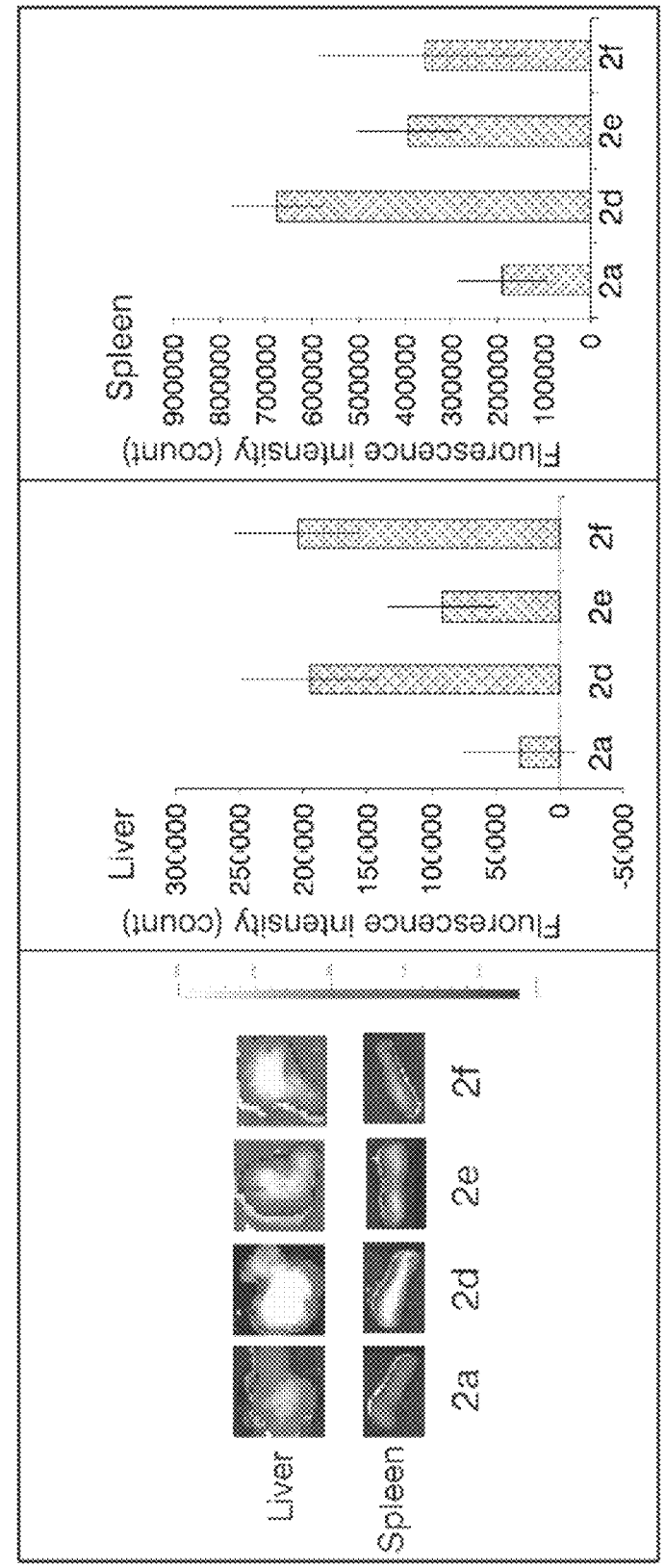

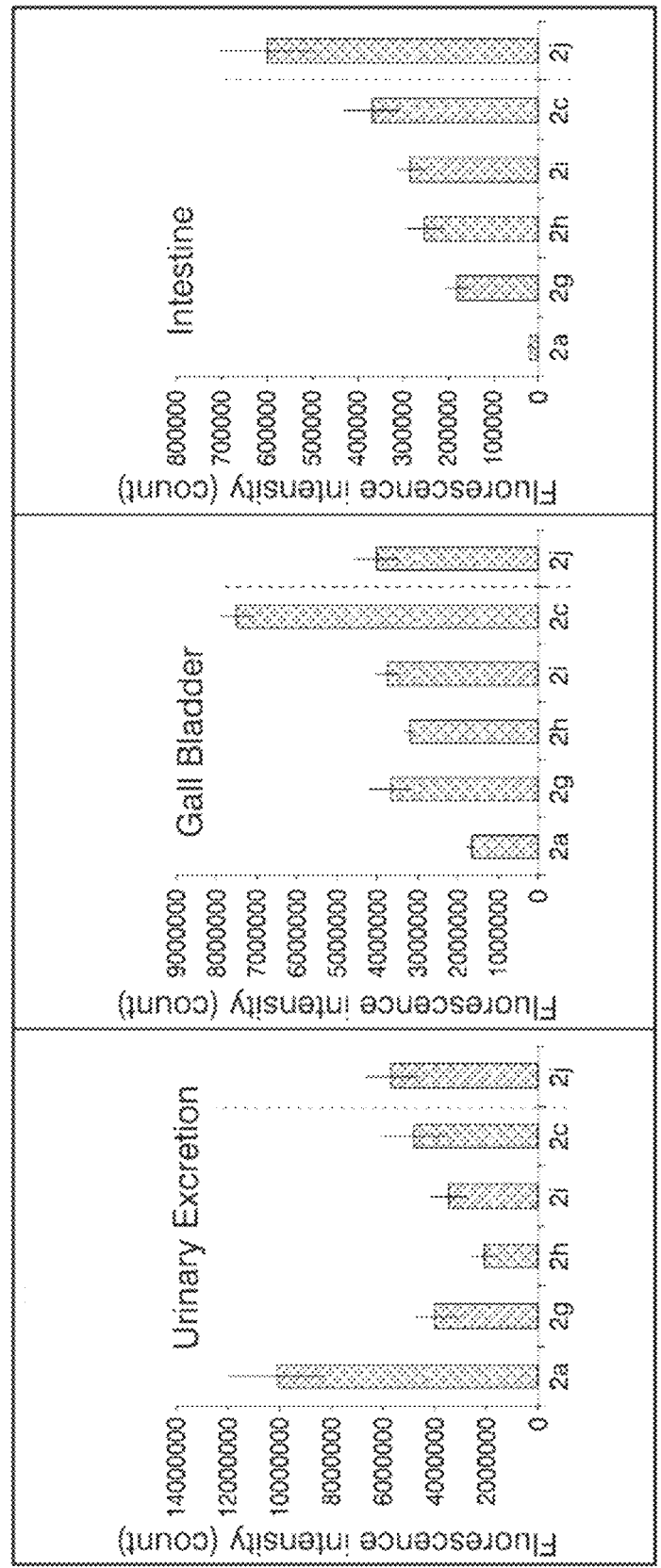

ALBUMIN-SUGAR CHAIN COMPLEX

TECHNICAL FIELD

The present application claims priority on the basis of Japanese Patent Application No. 2015-132002, filed on Jun. 30, 2015. The present application incorporates the contents of this basic application, along with the contents of documents cited therein, by reference.

The present invention relates to an albumin-sugar chain complex that is present in the body in a stable form and is capable of demonstrating a sugar chain clustering effect with a single molecule.

BACKGROUND ART

Asparagine-linked sugar chains (also abbreviated as "N-linked sugar chains") are composed of a structure in which a sugar chain is bound to an amide nitrogen atom of the side chain of asparagine (Asn), and may have a wide range of structures depending on such factors as the types and arrangement of monosaccharides composing the sugar chain or the presence or absence of branching. N-linked sugar chains are intimately involved in various biological functions, such as immune response regulation, cell growth, malignant transformation or metastasis of cancer cells, through interaction with other molecules such as proteins or lipids, while also contributing to stability of proteins in the body. Since the functions of these N-linked sugar chains can be expected to lead to applications in pharmaceuticals for diagnosis and treatment, analyses are being conducted on the pharmacokinetics of these N-linked sugar chains in the body. Since the interaction between N-linked sugar chains and proteins is mainly dependent on sugar chain structure, methods used to analyze the functions of N-linked sugar chains consist of administering a glycoprotein, obtained by binding an N-linked sugar chain having a specific sugar chain structure to a protein such as albumin, to an animal and analyzing parameters such as pharmacokinetics or the presence or absence of accumulation in tissue (see, for example, Non-Patent Document 1 or 2). In addition, N-linked sugar chains are also investigated non-invasively by further introducing a fluorescent substance into a glycoprotein having an N-linked sugar chain of a specific structure and analyzing the pharmacokinetics of the glycoprotein in the body of the animal by, for example, bioimaging (see, for example, Non-Patent Document 3).

Although the interaction between a single sugar chain and a protein is weak, a strong interaction is demonstrated when multiple sugar chains accumulate (sugar chain clustering effect). Consequently, in order to obtain this sugar chain clustering effect, complexes obtained by binding as many N-linked sugar chains as possible to a single protein molecule are preferable for use as glycoproteins used for functional analysis of N-linked sugar chains.

The inventors of the present invention previously reported that pharmacokinetics were analyzed by introducing 4 to 16 molecules of N-linked sugar chains per protein molecule into a polylysine skeleton and further synthesizing a sugar chain cluster in which the terminals thereof were modified with a fluorescent substance (see Non-Patent Document 4). Since sugar chains are bulky and have numerous hydroxy groups, it has conventionally been extremely difficult to increase the number of sugar chain molecules bound to a single protein molecule.

PRIOR ART DOCUMENTS

Patent Documents

[Patent Document 1] International Publication No. WO 2008/096760
[Patent Document 2] Japanese Unexamined Patent Application, First Publication No. 2015-030702

Non-Patent Documents

[Non-Patent Document 1] Andre, et al., Bioconjugate Chemistry, 1997, Vol. 8, p. 845-855
[Non-Patent Document 2] Unverzagt, et al., Journal of Medicinal Chemistry, 2002, Vol. 45, p. 478-491
[Non-Patent Document 3] Ogura, et al., Glycoconjugate Journal, 2014, Vol. 31, p. 273-279
[Non-Patent Document 4] Tanaka, et al., Angewandte Chemie International Edition, 2010, Vol. 49, p. 8195-8200

DISCLOSURE OF THE INVENTION

Problems to be Solved by the Invention

Sugar chain clusters having 16 molecules of N-linked sugar chains introduced per molecule of polylysine are susceptible to degradation when administered into the body. In addition, in the case of actually using as a pharmaceutical for diagnosis and treatment of humans, it is more preferable to use natural type proteins whenever possible.

An object of the present invention is to provide an albumin-sugar chain complex bound with a number of sugar chains sufficient for obtaining a sugar chain clustering effect while also being able to exist comparatively stably in the body.

Means for Solving the Problems

As a result of conducting extensive studies to solve the aforementioned problems, the inventors of the present invention found that, albumin has numerous lysine residues suitable for glycosylation, that the glycosylated form can exist comparatively stably in the body, and that the use of a newly developed "RIKEN click" reaction (6π-azaelectrocyclic reaction of a conjugated imine) (see, Patent Documents 1 and 2) enabled a large number of N-linked sugar chains to be introduced per molecule of albumin, thereby leading to completion of the present invention.

Namely, the albumin-sugar chain complex, functional molecule carrier and bioimaging probe according to the present invention are as indicated in [1] to [11] below.

[1] An albumin-sugar chain complex comprising five or more molecules of an asparagine-linked sugar chain bound per molecule of albumin.

[2] The albumin-sugar chain complex of [1] above, wherein the sugar on a non-reducing terminal of the asparagine-linked sugar chain comprises a sugar selected from the group consisting of N-acetylglucosamine, galactose, mannose and sialic acid.

[3] The albumin-sugar chain complex of [1] or [2] above, wherein the asparagine-linked sugar chain is one or more types of a sugar selected from the group consisting of the following formulas (a') to (f'):

[Chemical Formula 1]

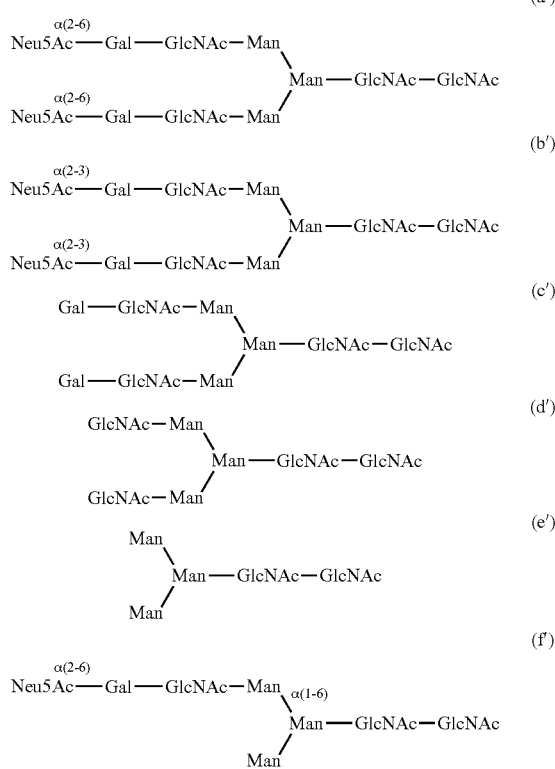

(wherein, NeuSAc represents N-acetylneuraminic acid, Gal represents galactose, GlcNAc represents N-acetylglucosamine and Man represents mannose).

[4] The albumin-sugar chain complex of any of [1] to [3] above, wherein the asparagine-linked sugar chain is bound to a lysine residue of albumin.

[5] A functional molecule carrier for selectively delivering a functional molecule to a target tissue in the body, which comprises the albumin-sugar chain complex of any of [1] to [4] above.

[6] A functional molecule carrier for selectively delivering a functional molecule to a target tissue in the body, comprising the albumin-sugar chain complex of [1] or [2] above, wherein the target tissue is hepatic stellate cells, and the non-reducing terminal of the asparagine-linked sugar chain is N-acetylglucosamine.

[7] A functional molecule carrier for selectively delivering a functional molecule to a target tissue in the body, comprising the albumin-sugar chain complex of [1] or [2] above, wherein the target tissue is hepatic Kupffer cells, and the asparagine-linked sugar chain is branched and has mannose and N-acetylneuraminic acid at its non-reducing terminal.

[8] A functional molecule carrier for selectively delivering a functional molecule to a target tissue in the body, comprising the albumin-sugar chain complex of [1] or [2] above, wherein the target tissue is the liver or spleen, and the non-reducing terminal of the asparagine-linked sugar chain is mannose.

[9] A functional molecule carrier for selectively delivering a functional molecule to a target tissue in the body, comprising the albumin-sugar chain complex of [1] or [2] above, wherein the target tissue is cancer cells, and the non-reducing terminal of the asparagine-linked sugar chain is α(2-3)-linked sialic acid.

[10] The functional molecule carrier of any of [5] to [9] above, wherein the functional molecule is a fluorescent substance or drug.

[11] A bioimaging probe comprising the albumin-sugar chain complex of any of [1] to [4] above as an active ingredient thereof that is administered into the body of an animal.

Effects of the Invention

The albumin-sugar chain complex according to the present invention is able to exist comparatively stably in the body, demonstrates a sugar chain clustering effect, and interacts strongly with other biomolecules such as proteins.

Consequently, the albumin-sugar chain complex according to the present invention is useful as a tool for analyzing the function of N-linked sugar chains, while also being useful as a functional molecule carrier for delivering a functional molecule to a specific cell or tissue, a bioimaging probe for labeling a specific cell or tissue, or an active ingredient of a pharmaceutical targeted at specific cells and the like.

BRIEF DESCRIPTION OF THE DRAWINGS

FIGS. 5A-5C respectively depict fluorescence images in the liver and spleen excised from mice individuals at 3 hours after administration of various complexes (FIG. 5A), a graph indicating the results of measuring fluorescence intensity in the liver (FIG. 5B), and a graph indicating the results of measuring fluorescence intensity in the spleen (FIG. 5C), in a Test Example 1.

FIGS. 6A-6C respectively depict graphs showing the results of measuring the amount of albumin-sugar chain complex excreted into urine for individual mice (FIG. 6A), the results of measuring fluorescence intensity in the gallbladder at 3 hours after administration of albumin-sugar chain complex for individual mice (FIG. 6B), and the results of measuring fluorescence intensity in the small intestine at 3 hours after administration of albumin-sugar chain complex for individual mice (FIG. 6C), in a Test Example 2.

EMBODIMENTS FOR CARRYING OUT THE INVENTION

Figure 1:
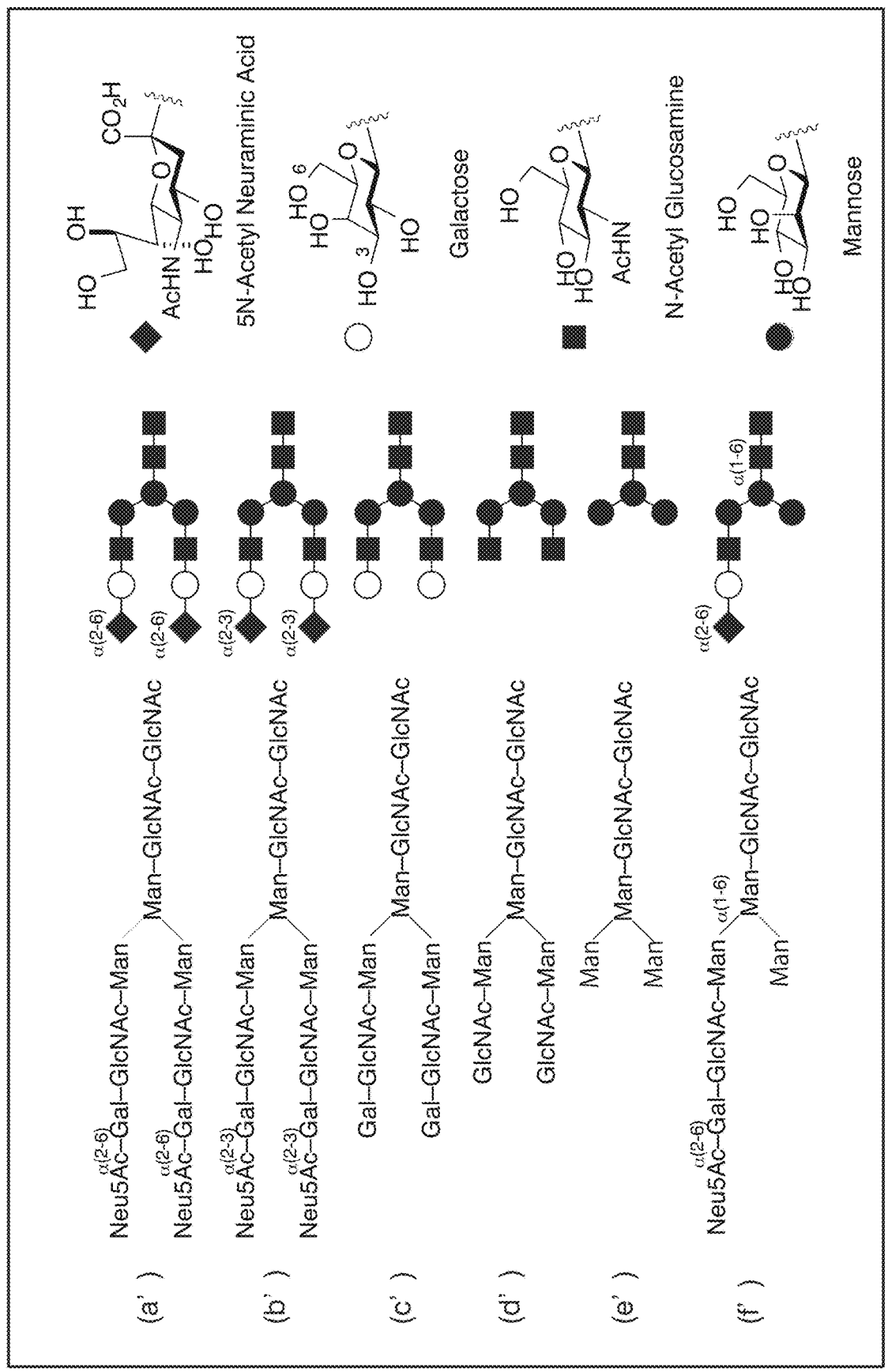
FIG. 1 is a schematic diagram of biantennary sugar chains represented by formulas (a') to (f').
Figure 2A:
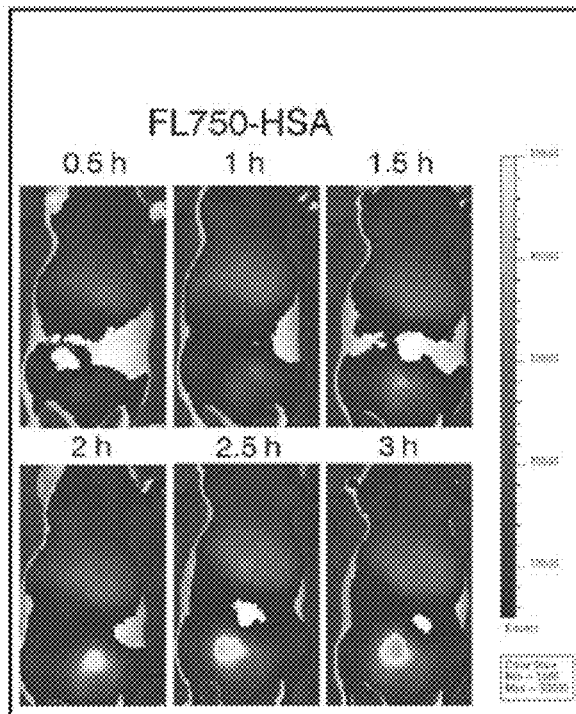
FIGS. 2A-2C respectively depict fluorescence images of mouse individuals at 0.5 hours to 3 hours after administration: mouse administered HL750-HSA (FIG. 2A), mouse administered a complex 2a (FIG. 2B), mouse administered a complex 2b (FIG. 2C), and mouse administered a complex 2c (FIG. 2D), in a Test Example 1.
Figure 2B:
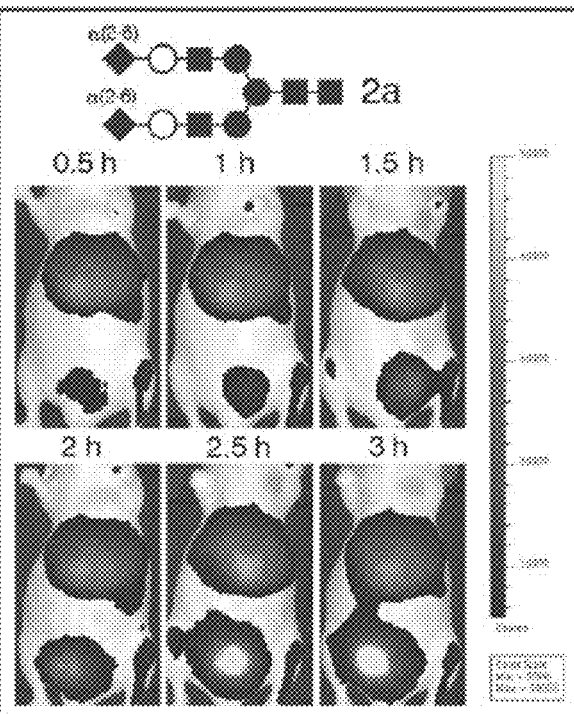
Figure 2C:
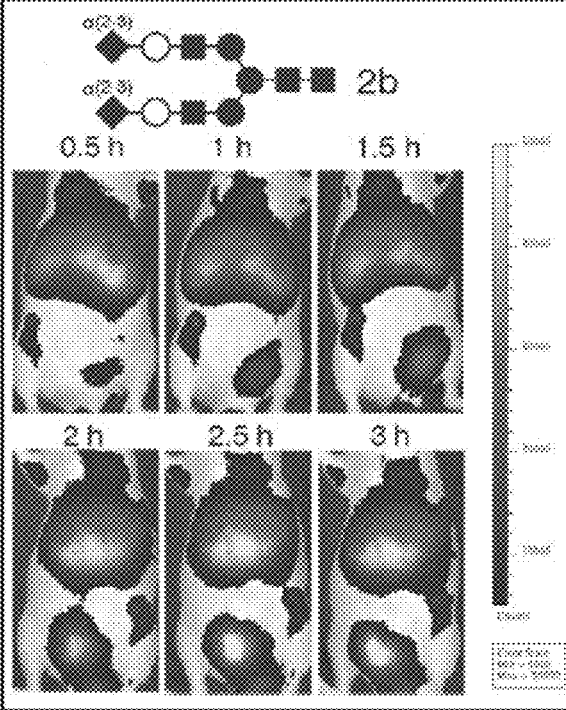
Figure 2D:
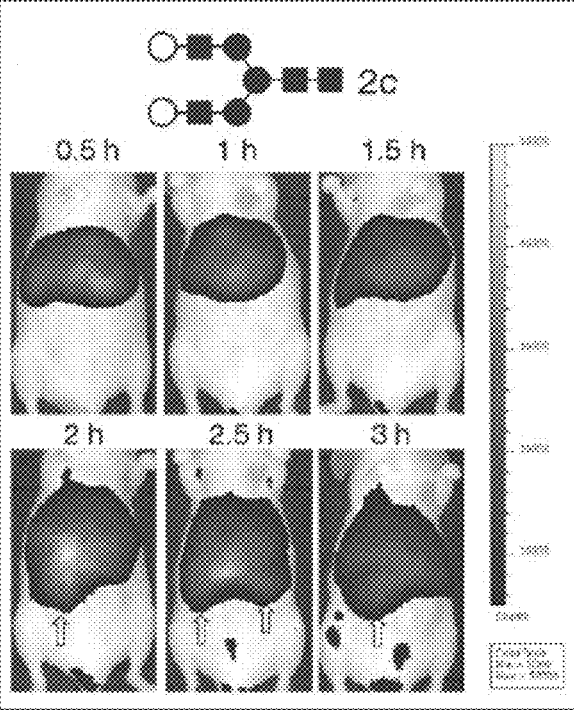

The albumin-sugar chain complex according to the present invention is characterized in that it comprises five or more molecules of N-linked sugar chains bound per molecule of albumin. A sugar chain complex having only one sugar chain molecule bound to a single albumin molecule exhibits weak interaction between the sugar chain and other molecules such as proteins and has low reactivity. In contrast, the albumin-sugar chain complex according to the present invention comprises five or more molecules of N-linked sugar chains bound per molecule, thereby enabling the complex to demonstrate an adequate sugar chain clustering effect even in the case of a single molecule thereof, while also resulting in strong interaction between the sugar chain and a specific biomolecule. The albumin-sugar chain complex according to the present invention preferably comprises nine or more molecules of N-linked sugar chains per molecule of albumin. Although there are no particular limitations thereon, the upper limit of the number of N-linked sugar chains can be, for example, 30 molecules or less, preferably 20 molecules or less, more preferably 15 molecules or less, and even more preferably 11 molecules or less.

The albumin-sugar chain complex according to the present invention uses albumin for the protein that binds the N-linked sugar chain. The N-linked sugar chain is linked to a lysine residue of albumin. Albumin demonstrates superior stability in the body and has numerous lysine residues suitable for glycosylation. For example, human albumin has roughly 60 lysine residues per molecule, and 10 to 30 of these are presumed to be lysine residues capable of glycosylation. In addition, albumin also offers the advantages of resisting the acquisition of antigenicity and being less likely to be metabolized as a foreign body in the body even after having been glycosylated.

The albumin that constitutes the albumin-sugar chain complex according to the present invention may be a natural type protein purified from an animal or may be a recombinant. In addition, the albumin may be wild-type albumin inherently possessed by any animal, or may be a mutant albumin in which one or a plurality of amino acids other than lysine residues present in wild-type albumin have been deleted, substituted or added.

The albumin that constitutes the albumin-sugar chain complex according to the present invention is preferably serum albumin and more preferably serum albumin derived from a mammal. Preferable examples of mammals include humans, mice, rats, rabbits, guinea pigs, hamsters, monkeys, sheep, horses, cows, pigs, donkeys, dogs, cats and other domestic or laboratory animals, with humans being particularly preferable.

The N-linked sugar chain that constitutes the albumin-sugar chain complex according to the present invention may consist of only one type of sugar chain or may consist of two or more types of sugar chains. In addition, there are no particular limitations on the sugar that constitutes a single molecule of the N-linked sugar chain provided it is a monosaccharide (monosaccharide or derivative thereof) capable of forming a chain structure by glycosidic linkages, and may be a monosaccharide composed of one type of monosaccharide or monosaccharide composed of two or more types of monosaccharides.

Examples of these monosaccharides include glucose (Glu), galactose (Gal), mannose (Man), N-acetylglucosamine (GlcNAc), N-acetylgalactosamine (GalNAc), fucose (Fuc), xylose (Xyl), glucuronic acid (GlcA), iduronic acid (IdoA), N-acetylneuraminic acid (Neu5Ac), N-glycolylneuraminic acid (Neu5Gc), deaminoneuraminic acid (KDN: 2-keto-3-deoxy-D-glycero-D-galactononoic acid) and derivatives thereof.

There are no particular limitations on the state of the glycosidic linkages, and may be, for example, α1,4 linkage, α1,6 linkage, α2,3 linkage, α2,6 linkages, β1,2 linkages or β1,4 linkages.

The N-linked sugar chains that constitutes the albumin-sugar chain complex according to the present invention preferably comprises a consensus sequence consisting of
*-Man-GlcNAc-GlcNAc- (wherein,  represents the side bound to albumin).

In the albumin-sugar chain complex according to the present invention, the sugar chain moiety of the N-linked sugar chains bound to one molecule of albumin may be linear or branched. The sugar chains that constitutes the albumin-sugar chain complex according to the present invention are preferably biantennary sugar chains present in comparatively large amounts in the body of an animal, and are preferably one or more types selected from the group consisting of formulas (a') to (f') shown in FIG. 1. Furthermore, the sugar chains of formulas (a') to (f') are present in large amounts in the bodies of humans and other animals.

[Chemical Formula 2]

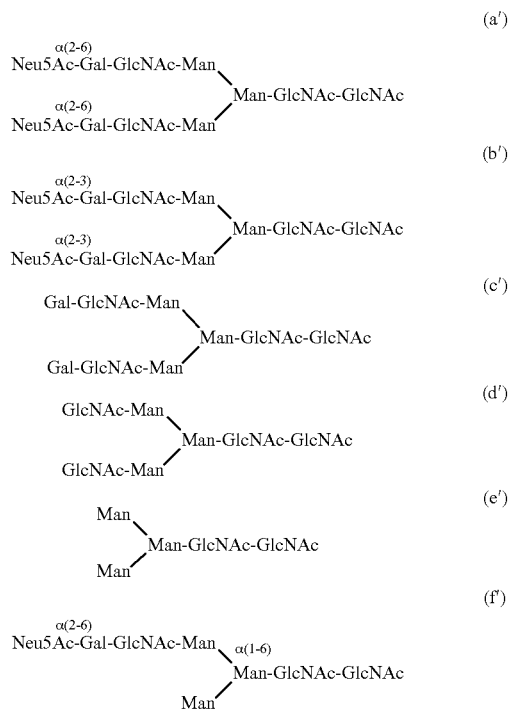

For example, the use of a compound described in Patent Documents 1 and 2 makes it possible to link five or more molecules of N-linked sugar chains per molecule of albumin. More specifically, an aldehyde compound containing an N-linked sugar chain represented by the following general formula (I-0) is linked to a lysine residue of albumin by the reaction indicated below. This reaction is carried out on the side chains of at least five lysine residues on the surface of albumin. The albumin-sugar chain complex synthesized in this manner has five or more structures represented by the following general formula (I) per molecule of albumin.

[Chemical Formula 3]

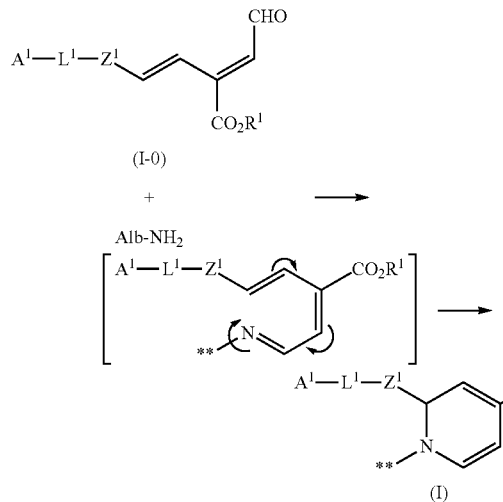

(I-0)

In general formula (I) and general formula (I-0), $A^1$ represents N-linked sugar chain-Asn- (group in which an N-linked sugar chain is bound to an amide nitrogen atom of a side chain of an Asn residue). The sugar chain present in $A^1$ is preferably a sugar chain represented by the aforementioned formulas (a') to (f'). In addition, $L^1$ is bound to a nitrogen atom not bound to the sugar chain of the Asn residue present in $A^1$.

In general formula (I), ** represents the site that binds to a carbon atom bound to an amino group on a side chain of a lysine residue of albumin. In addition, Alb-NH, represents albumin.

In general formula (I) and general formula (I-0), $R^1$ represents an alkyl group having 1 to 6 carbon atoms. This alkyl group may be linear or branched. Examples of this alkyl group include a methyl group, ethyl group, propyl group, isopropyl group, n-butyl group, isobutyl group, t-butyl group, pentyl group, isoamyl group and hexyl group. In the case of the albumin-sugar chain complex according to the present invention, $R^1$ in general formula (I) is preferably an alkyl group having 1 to 3 carbon atoms, more preferably a methyl group, ethyl group or propyl group, and even more preferably an ethyl group.

In general formula (I) and general formula (I-0), $Z^1$ represents a 1,2-phenylene group, 1,3-phenylene group or 1,4-phenylene group. In the case of the albumin-sugar chain complex according to the present invention, $Z^1$ in general formula (I) preferably represents a 1,4-phenylene group.

In general formula (I) and general formula (I-0), $L^1$ represents an arbitrary linking group. Although there are no particular limitations on $L^1$ provided it is a divalent group that does not inhibit the RIKEN click reaction, since a higher degree of freedom of movement of the N-linked sugar chain linked to albumin makes it easier to demonstrate the sugar chain clustering effect, a group having a comparatively long chain or a bulky group, such as that having a ring structure, is preferable.

$L^1$ in general formula (I) and general formula (I-0) is preferably a group represented by the following general formula (II). In general formula (II), $R^2$ represents an alkylene group having 1 to 20 carbon atoms and $L^2$ represents an arbitrary linking group. In general formula (II), * represents the site that binds to $A^1$ in the aforementioned general formula (I), while ** represents the site that binds to $Z^1$ in the aforementioned general formula (I).

[Chemical Formula 4]

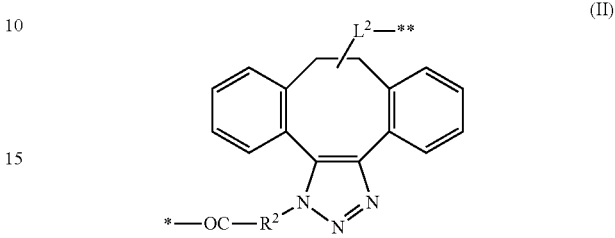

The alkylene group represented by $R^2$ may be linear or branched. As a result of increasing the degree of freedom of movement of the N-linked sugar chain by linking albumin and the N-linked sugar chain with a flexible alkylene group, a plurality of N-linked sugar chains bound to the same albumin molecule mutually accumulate more easily. Examples of this alkylene group include a methylene group, ethylene group, propylene group, isopropylene group, n-butylene group, isobutylene group, pentylene group, hexylene group, heptylene group, octylene group, nonylene group, decylene group, undecylene group, dodecylene group, tridecylene group, tetradecylene group, pentadecylene group, hexadecylene group, heptadecylene group and nonadecylene group. In the case of the albumin-sugar chain complex according to the present invention, $R^2$ of general formula (II) preferably represents an alkylene group having 3 to 10 carbon atoms, more preferably represents a linear alkylene group having 3 to 10 carbon atoms, and even more preferably represents a linear alkylene group having 4 to 8 carbon atoms.

There are no particular limitations on $L^2$ in general formula (II) provided it is a divalent group that does not inhibit the RIKEN click reaction. Specific examples of $L^2$ include —O—CO—NH— $(CH_2)_n$—CO—NH—, —O—CO—NH—$(CH_2)_n$—NH—CO—, —$(CH_2)_n$—, —$(CH_2)_n$—O—$(CH_2)_m$—, —$(CH_2)_n$—CO—NH— and —$(CH_2)_n$—NH—CO— (wherein, n and m respectively and independently represent an integer of 1 to 20).

An aldehyde compound (I'-0), in which $L^2$ in general formula (I-0) represents a group represented by general formula (II), can be synthesized by a cyclization reaction between an azide represented by the following general formula (III) and an aldehyde represented by the following general formula (IV) (alkyne-azide cyclization). In general formulas (III) and (IV), $A^1$, $Z^1$ and $R^2$ are the same as in general formula (I), while $L^2$ and $R^2$ are the same as in general formula (II).

[Chemical Formula 5]

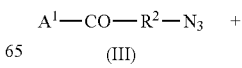

(III)

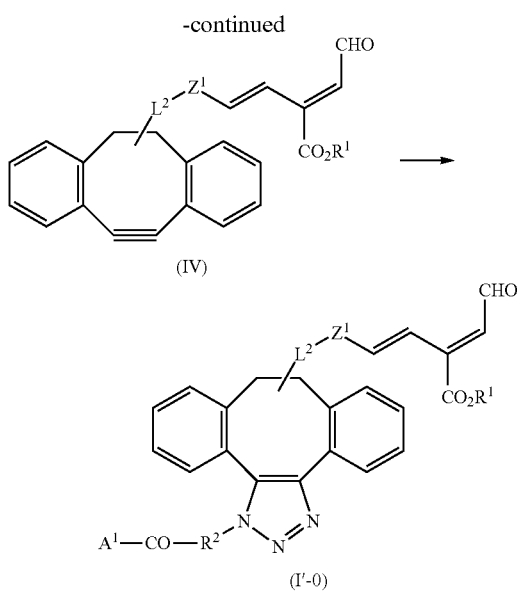

This cyclization reaction can be carried out by, for example, mixing both substances in a polar solvent in a nitrogen atmosphere. Examples of polar solvents include water, dimethylformamide (DMF), dimethylsulfoxide (DMSO), methyl cyanide (acetonitrile), propionitrile, dimethoxyethane (DME) and mixed solvents thereof. The reaction is preferably carried out at a temperature of 50° C. or higher, more preferably at a temperature of 60° C. to 100° C., and even more preferably at a temperature of 60° C. to 80° C.

The albumin-sugar chain complex according to the present invention preferably has a structure represented by the following general formulas (V-1) to (V-8). In general formulas (V-1) to (V-8), $R^1$ is the same as $R^1$ in the aforementioned general formula (I), $R^2$ is the same as $R^2$ in the aforementioned general formula (II), n1 represents an integer of 1 to 6, * represents the binding site with a sugar chain, and ** represents the site that binds to a carbon atom bound to an amino group of a side chain of a lysine residue of albumin. The sugar chain bound at * is preferably that represented by any of the aforementioned formulas (a') to (f').

Compounds represented by the following general formulas (V-1) to (V-8) are preferably compounds in which $R^1$ represents an alkyl group having 1 to 3 carbon atoms, $R^2$ represents an alkylene group having 3 to 16 carbon atoms, n1 represents an integer of 1 to 3 and the sugar chain bound at * is any of those represented by the aforementioned formulas (a') to (f'), and more preferably compounds in which $R^1$ represents an alkyl group having 1 to 3 carbon atoms, $R^2$ represents an alkylene group having 3 to 10 carbon atoms, n1 represents an integer of 1 to 3, and the sugar chain bound at * is any of those represented by the aforementioned formulas (a') to (f').

[Chemical Formula 6]

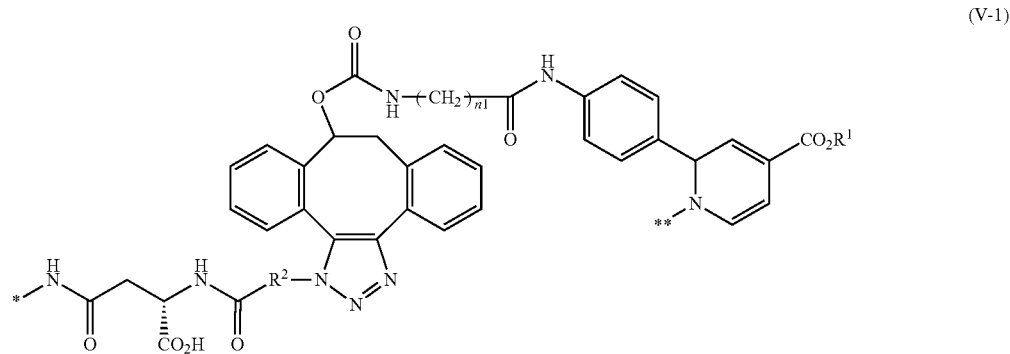

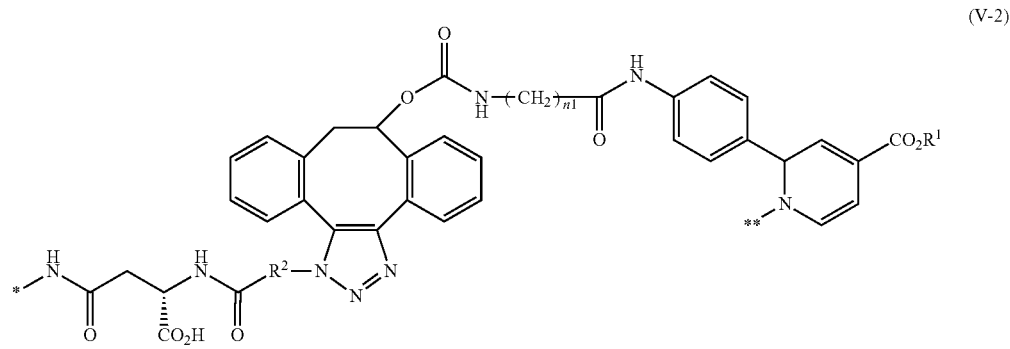

(V-3)
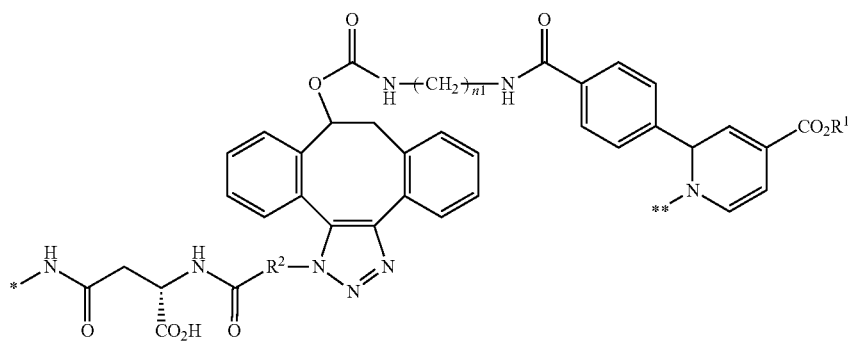
(V-4)
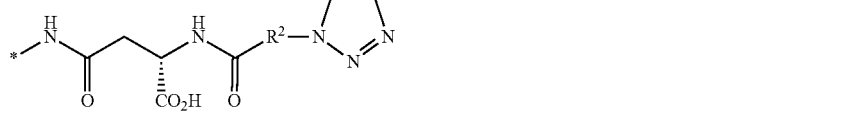
[Chemical Formula 7]
(V-5)
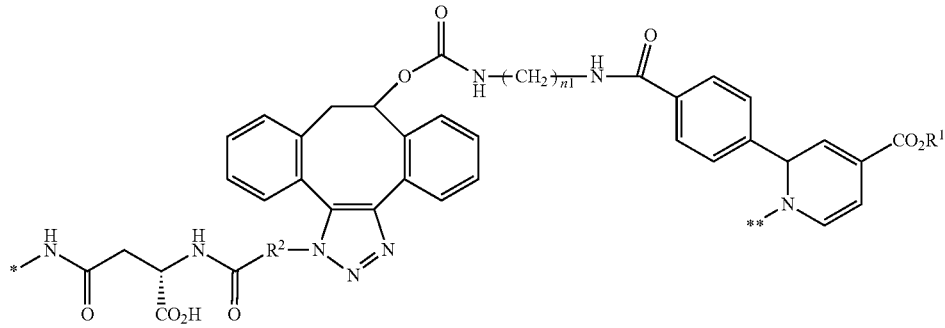
(V-6)
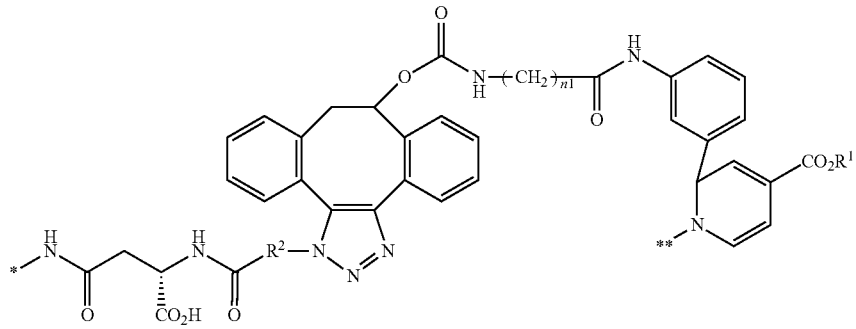

(V-7)

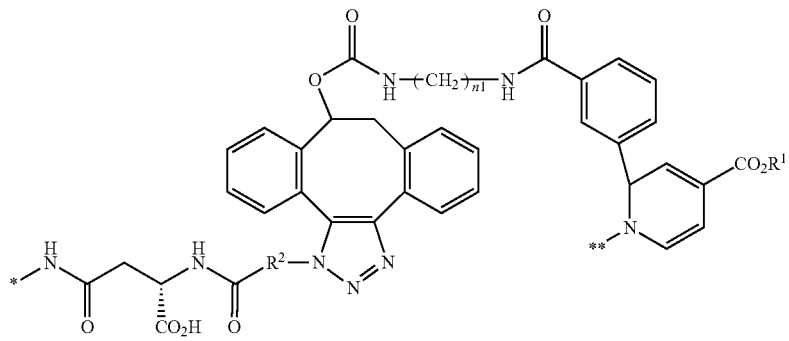

(V-8)

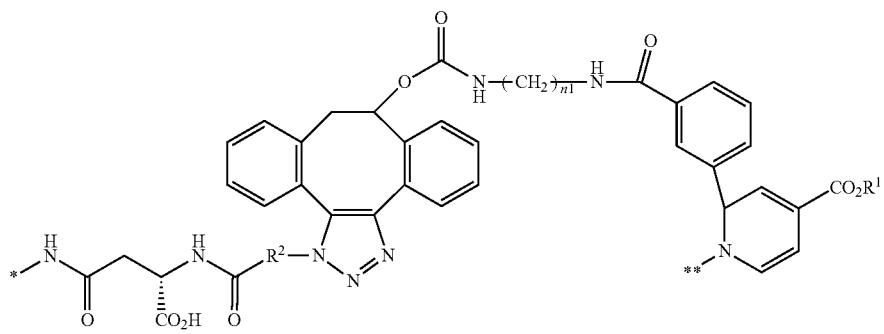

The RIKEN click reaction between an aldehyde compound represented by the aforementioned general formula (I-0) and albumin can be carried out by, for example, mixing both substances in a polar solvent.

Examples of polar solvents include water, dimethylformamide (DMF), dimethylsulfoxide (DMSO), methyl cyanide, propionitrile, dimethoxyethane (DME) and mixed solvents thereof. The reaction is preferably carried out at a temperature of 60° C. or lower, more preferably at a temperature of 50° C. or lower, and even more preferably at a temperature of 15° C. to 40° C. so not denature the albumin.

The number of molecules of N-linked sugar chains introduced into a molecule of albumin can be adjusted by adjusting the molar ratio between the aldehyde compound represented by the aforementioned general formula (I-0) and albumin used in the aforementioned RIKEN click reaction. The greater the amount of the aforementioned aldehyde compound relative to albumin, the greater the number of molecules of N-linked sugar chains that can be introduced into one molecule of albumin.

In the case of introducing two or more types of N-linked sugar chains into one molecule of albumin, each aldehyde compound represented by general formula (I-0) containing an N-linked sugar chain is sequentially reacted with albumin. N-linked sugar chains are sequentially introduced in order starting with the lysine residue among the plurality of lysine residues on the surface of albumin that reacts most easily with the aldehyde compound. Consequently, depending on the order in which N-linked sugar chains are reacted with albumin, albumin-sugar chain complexes having different reactivity with other proteins may be obtained even if the number of molecules of each N-linked sugar chain bound per molecule of albumin is the same.

The albumin-sugar chain complex according to the present invention preferably contains a labeling substance or a binding site for binding with a labeling substance. The albumin-sugar chain complex can be detected with this labeling substance. The labeling substance is preferably a labeling substance that enables detection of an albumin-sugar chain complex administered into the body, and examples thereof include fluorescent substances, substances having a structure that coordinates with a radioactive metal, substances containing a radioisotope, and substances having a structure that coordinates with a paramagnetic substance used for MRI. These labeling substances are preferably bound to a moiety other than the N-linked sugar chain in the albumin-sugar chain complex.

There are no particular limitations on the fluorescent substance retained by the albumin-sugar chain complex according to the present invention, and a fluorescent substance can be used that has been suitably selected from among fluorescent substances used during fluorescent labeling of proteins or sugars and the like. The fluorescent substance may be a protein, a pigment or a quantum dot. The fluorescent substance contained by the albumin-sugar chain complex according to the present invention is preferably that which can be administered into the body comparatively safely, and more preferably a near-infrared fluorescent substance since the albumin-sugar chain complex within the body is detected more easily outside the body. Examples of near-infrared fluorescent substances include organic fluorescent dyes having an indocyanine skeleton such as HiLyte Fluor® 750, indocyanine green, Alexa Fluor® 647, Alexa Fluor 680, Alexa Fluor 790, Cy® 3.5, Cy 5, Cy 5.5 and Cy 7, cyanine derivatives such as brilliant blue or brilliant green, and inorganic nanoparticles such as $Y_2O_3$ fluorescent nanoparticles.

Among the labeling substances retained by the albumin-sugar chain complex according to the present invention, examples of substances having a structure that coordinates with a radioactive metal include DOTA (1,4,7,10-tetraaza-cyclodecane-1,4,7,10-tetraacetic acid) and DTPA (diethylenetriamine pentaacetic acid). Examples of the aforementioned substances containing a radioisotope include derivatives containing one or more types of radioisotopes selected from the group consisting of $^{18}F$, $^{11}C$, $^{13}N$, $^{15}O$ and $^{99m}Tc$ (such as trifluoro($^{18}F$)borate). An example of the aforementioned substances having a structure that coordinates with a paramagnetic substance used for MRI is gadolinium.

The albumin-sugar chain complex according to the present invention may also contain a tag peptide or low molecular weight substance such as biotin. Examples of this tag peptide include His tag, Flag tag and HA tag. Isolation and purification from a mixture can be carried out easily by containing such a substance that specifically binds with a specific substance.

Since the albumin-sugar chain complex according to the present invention has a large number of N-linked sugar chains in a single molecule thereof, specific interactions between the sugar chain and other substances appear more prominently than sugar chain complexes having only one N-linked sugar chain in a molecule thereof. Therefore, by utilizing the affinity between this sugar chain and another substance, the albumin-sugar chain complex according to the present invention can be used as a probe for detecting cells or tissue in which a substance having high affinity for the sugar chain contained therein is present on the surface thereof. In particular, since the albumin-sugar chain complex according to the present invention is comparatively stable in the body of an animal, it is useful as an active ingredient of a bioimaging probe administered into the body of an animal for the purpose of ascertaining the distribution or localization of a protein or other biomolecule at the cell, tissue or individual level, and analyzing the pharmacokinetics thereof in the form of an image.

For example, in the case of having administered the albumin-sugar chain complex according to the present invention to an animal, complexes in which the non-reducing terminal contains an N-linked sugar chain in the form of N-acetylglucosamine in the manner of the formula (d') accumulate in the liver and are taken up into stellate cells in particular through interaction with Desmin and Vimentin. Consequently, these albumin-sugar chain complexes are useful as bioimaging probes for detecting activated stellate cells in the liver in particular, or as functional molecule carriers for selectively delivering a functional molecule to stellate cells in particular. In addition, complexes in which the non-reducing terminal contains a biantennary N-linked sugar chain consisting of mannose and N-acetylneuraminic acid in the manner of formula (f') accumulate in the liver and are taken up by Kupffer cells in particular. Consequently, these albumin-sugar chain complexes are useful as functional molecule carriers for selectively delivering a functional molecule to Kupffer cells in particular. In addition, complexes in which the non-reducing terminal contains an N-linked sugar chain in the form of mannose in the manner of formula (e') accumulate mainly in the liver and spleen through interaction with C-type lectin present on Kupffer cells. Consequently, these albumin-sugar chain complexes are useful as bioimaging probes for detecting the liver or spleen, or as functional molecule carriers for selectively delivering a functional molecule to the liver or spleen. Moreover, complexes in which the non-reducing terminal contains an N-linked sugar chain in the form of α(2-3)-linked sialic acid (having a sialic acid-galactose linkage) in the manner of formula (b') accumulate in cancer cells through interaction with selectin highly expressed on the surface of cancer cells. Consequently, an albumin-sugar chain complex in which at least one molecule of the N-linked sugar chain per molecule of albumin is α(2-3)-linked sialic acid is useful as a bioimaging probe for detecting cancer or as a functional molecule carrier for selectively delivering a functional molecule to cancer cells. Furthermore, examples of functional molecules include radiation therapy drugs and diagnostic drugs. In the case of using the albumin-sugar chain complex according to the present invention as a functional molecule carrier, the functional molecule is preferably bound to a moiety other than the N-linked sugar chain in the albumin-sugar chain complex, and is more preferably bound to a moiety other than a lysine residue of albumin.

In addition, the albumin-sugar chain complex according to the present invention is also useful as an active ingredient of a pharmaceutical. For example, that in which an anticancer drug is bound to the albumin present in an albumin-sugar chain complex in which the non-reducing terminal contains an N-linked sugar chain in the form of α(2-3)-linked sialic acid can serve as an active ingredient of a pharmaceutical used to treat cancer.

The albumin-sugar chain complex according to the present invention enhances differences in physiological activity attributable to differences in sugar chain structure by a sugar chain clustering effect. Consequently, the albumin-sugar chain complex according to the present invention is also useful for analyzing functions as recognition signals in the vital phenomena of sugar chains. By administering an albumin-sugar chain complex containing a labeling substance into an animal and detecting that labeling substance, the pharmacokinetics of the albumin-sugar chain complex in the body, such as the elimination route thereof, can be analyzed. For example, although asialoglycoproteins present in the blood, in which the non-reducing terminal thereof is not sialic acid, are taken up into hepatocytes by binding with asialoglycoprotein receptors (ASGR) present on the surface of hepatocytes, sialoglycoproteins, in which the non-reducing terminal is sialic acid, are not taken up into hepatocytes despite binding with ASGR. In actuality, as is indicated in the examples to be subsequently described, although albumin-sugar chain complexes containing an N-linked sugar chain in which the non-reducing terminal is acidic sialic acid in the manner of formula (a') or formula (b') are metabolized and rapidly excreted from the urinary bladder via the kidneys, albumin-sugar chain complexes containing an N-linked sugar chain in which the non-reducing terminal is galactose in the manner of formula (c') have been determined to be excreted intestinally via the liver and gallbladder. The effects of other sugar chains on the excretion route of a particular substance can be similarly analyzed using the albumin-sugar chain complex according to the present invention.

EXAMPLES

The following provides a detailed explanation of the present invention by indicating examples thereof. However, the present invention is not limited by the following descriptions.

Furthermore, azide derivatives of N-linked sugar chains used in the following experiments represented by the following formulas (a) to (f) were all synthesized by GlyTech, Inc. using the method described in Angew. Chem. Int. Ed., Vol. 49, p. 8195-8200 (2010), and the aldehyde compound represented by the following formula (1) was synthesized using the method described in Org. Biomol. Chem., Vol. 12, p. 1412-1418 (2014).

In addition, in the following experiments, reversed-phase HPLC was carried out using a high-performance chromatography system (system name: Prominence® System, Shimadzu Corp.) equipped with a C18 column (trade name: 5C18-AR-300, 4.6×250 mm, Nacalai Tesque, Inc.). High-resolution mass spectra (HRMS) were obtained by ESI-TOF MS using a mass spectrometer (trade name: micrOTOF-QIII® Spectrometer, Bruker GmbH). Protein mass spectra were obtained by MALDI-TOF MS using a mass spectrometer (trade name: Autoflex® Spectrometer, Bruker GmbH).

[Production Example 1] Synthesis of HL750-HSA

A solution obtained by dissolving 0.25 mg (0.19 μmol) of near-infrared fluorescent dye HiLyte Fluor® 750 Acid SE (2× tetraethylammonium salt) in 10 μL of DMSO was added to an HSA solution obtained by dissolving 3.4 mg (48 nmol) of human serum albumin (HSA, purchased from Sigma Corp.) in 300 μL of PBS (phosphate-buffered saline, pH: 7.4) to prepare a reaction solution. After incubating the resulting reaction solution for 10 minutes at 37° C. to allow the near-infrared fluorescent dye to bind to the HSA, the reaction solution was centrifuged (15,000 rpm, 10 minutes) with the Amicon® 10K (Merck-Millipore Ltd.). The residue was further washed three times with phosphate buffer. A solution obtained by dissolving the resulting HL750-HSA (HSA bound to near-infrared fluorescent dye) in 800 μL of ultrapure water was used as an HL750-HSA stock solution. As a result of analyzing by MALDI-TOF MS, the average mass of the synthesized HL750-HSA was 70.5 kDa and 3.1 molecules of near-infrared fluorescent dye were bound per molecule thereof.

Example 1

HL750-HSA bound with the N-linked sugar chain represented by formula (a') (2,6-HLF-HSA, to be referred to as "Complex 2a") was synthesized.

<Synthesis of Aldehyde Compound Represented by Formula (1a)>

45 μL (0.45 μmol) of a solution of the aldehyde compound represented by formula (1), obtained by dissolving in methyl cyanide to a concentration of 10 mM in a nitrogen atmosphere, were added to a solution obtained by dissolving 1.24 mg (0.50 μmol) of an azide derivative of an N-linked sugar chain having a sugar chain represented by formula (a') (azide derivative represented by the following formula (a), GlyTech, Inc.) in 139 μL of DMSO. The resulting reaction solution was heated to 70° C. followed by confirming the reaction product by HPLC. After the initially added aldehyde compound was consumed, the reaction solution was cooled to room temperature to obtain a stock solution (3.8 mM) in which the aldehyde compound represented by the following formula (1a) is dissolved in DMSO. The synthesized aldehyde compound represented by formula (1a) was able to be detected by ESI-TOF MS (detected value of $C_{128}H_{183}N_{13}O_{71}$ $[M-2H]^{-2}/2$: 1518.0509, calculated value: 1518.0482).

[Chemical Formula 8]
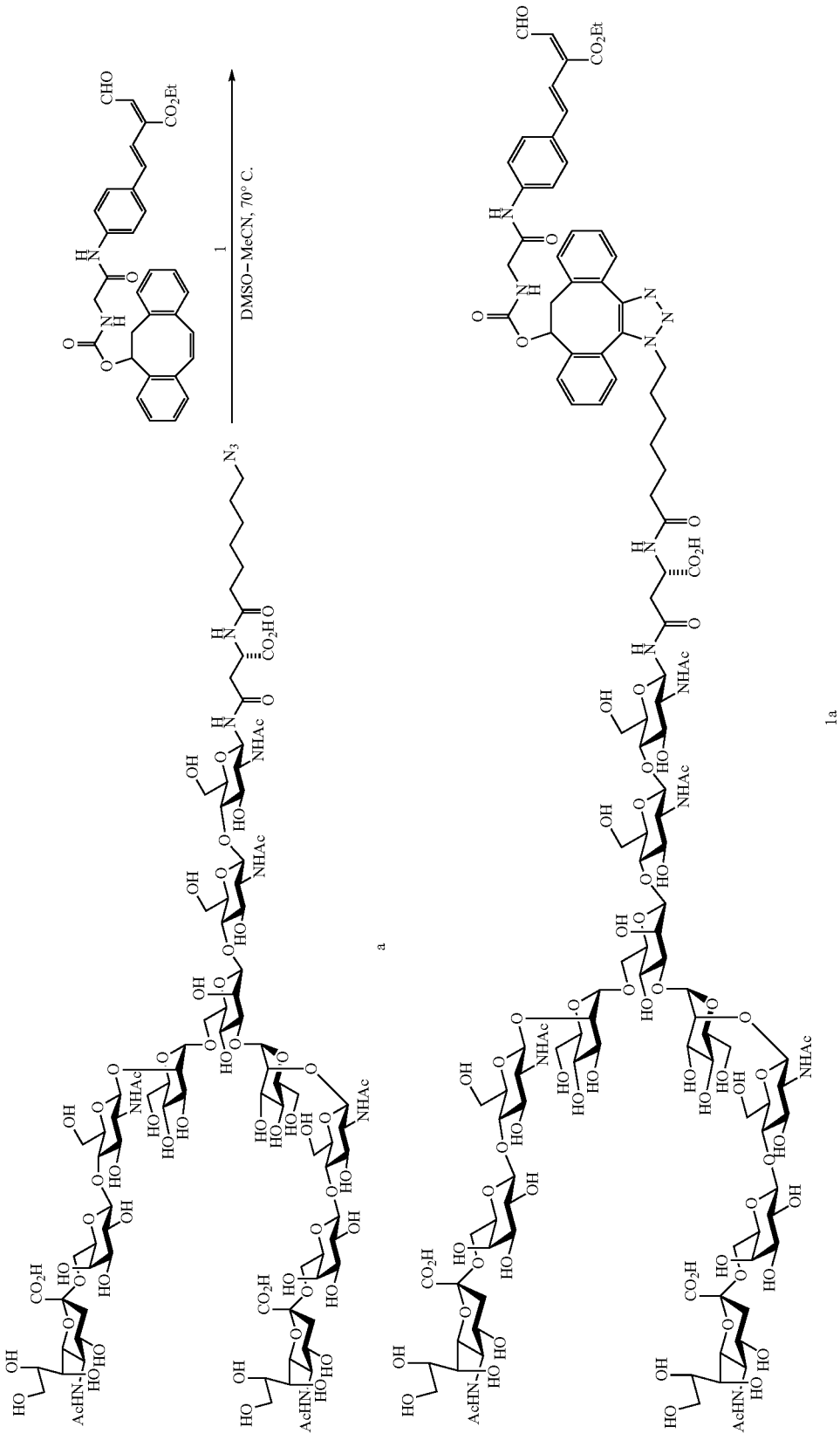

<Synthesis of Complex 2a>

132 μL of water, 66 μL of DMSO and 32 μL (0.12 μmol, 16 eq) of the stock solution of the aldehyde compound represented by formula (1a) (3.8 mM) were mixed with 132 μL (7.5 nmol) of the HL750-HSA stock solution synthesized in Production Example 1 to prepare a reaction solution. The resulting reaction solution was allowed to react by incubating while gently stirring overnight at 37° C. in an air atmosphere to synthesize Complex 2a. After filtering the resulting reaction product with the Amicon 10K, the reaction product was washed three times with water. Subsequently, the reaction solution was filtered with a Durapore® PVDF membrane (0.45 km) followed by diluting to 150 μL with water to prepare a Complex 2a solution. As a result of analyzing by MALDI-TOF MS, the average mass of the synthesized Complex 2a was 98.0 kDa and 9.2 molecules of N-linked sugar chain (aldehyde compound represented by formula (1a)) were bound per molecule thereof.

Example 2

HL750-HSA bound with the N-linked sugar chain represented by formula (b') (2,3-HLF-HSA, to be referred to as "Complex 2b") was synthesized.

<Synthesis of Aldehyde Compound represented by Formula (1b)>54 μL (0.54 μmol) of a solution of the aldehyde compound represented by formula (1), obtained by dissolving in methyl cyanide to a concentration of 10 mM in a nitrogen atmosphere, were added to a solution obtained by dissolving 1.48 mg (0.59 μmol) of an azide derivative of an N-linked sugar chain having a sugar chain represented by formula (b') (azide derivative represented by the following formula (b), GlyTech, Inc.) in 144 μL of DMSO. The resulting reaction solution was heated to 70° C. followed by confirming the reaction product by HPLC. After the initially added aldehyde compound was consumed, the reaction solution was cooled to room temperature to obtain a stock solution (3.8 mM) in which the aldehyde compound represented by the following formula (1b) is dissolved in DMSO. The synthesized aldehyde compound represented by formula (1b) was able to be detected by ESI-TOF MS (detected value of $C_{128}H_{183}N_{13}O_{71}$ $[M-2H]^{-2}/2$: 1518.0460, calculated value: 1518.0482).

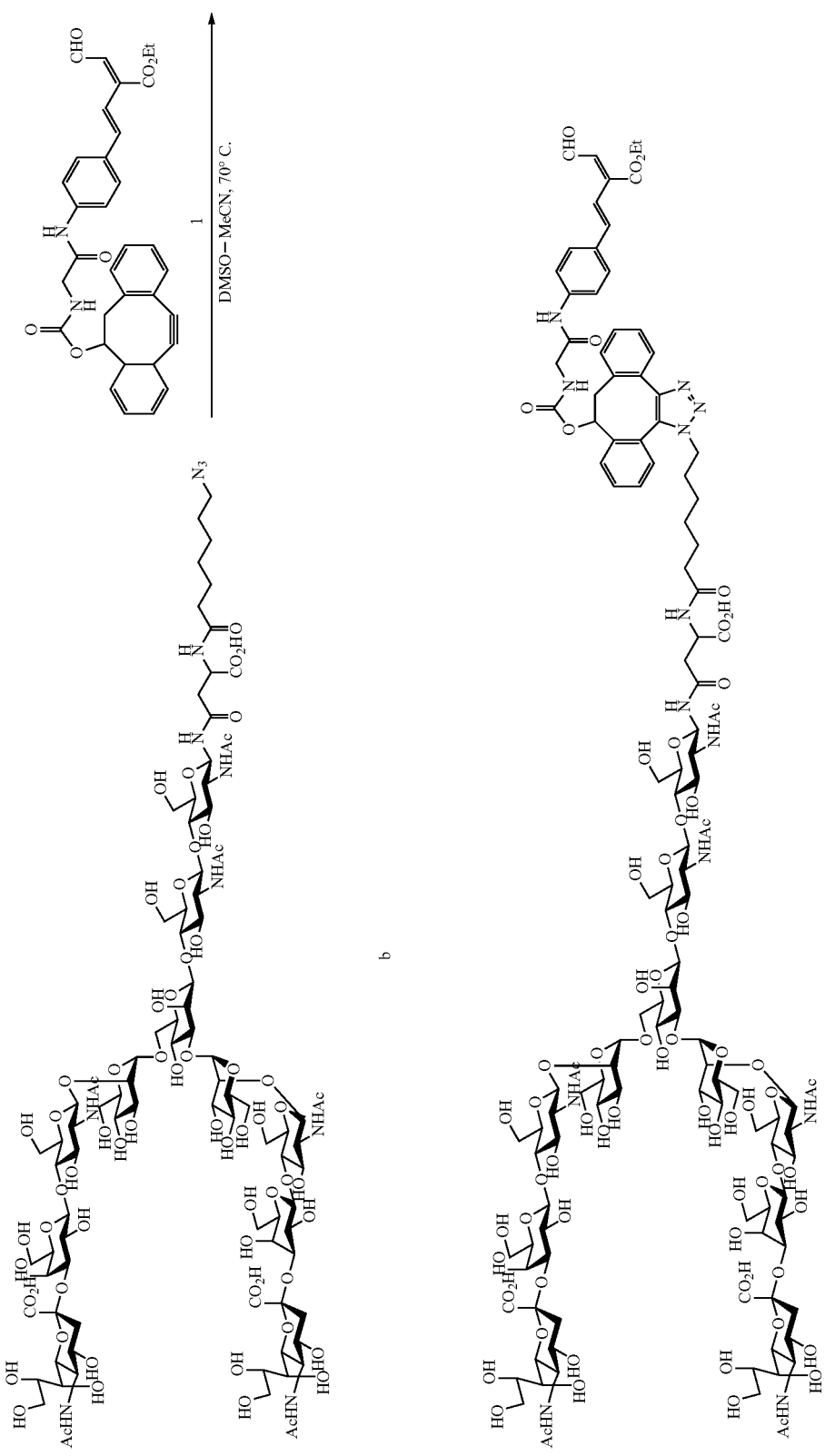

<Synthesis of Complex 2b>

52.5 µL of water, 26.2 µL of DMSO and 24 µL (90 nmol, 30 eq) of the stock solution of the aldehyde compound represented by formula (1a) (3.8 mM) were mixed with 52.5 µL (3.0 nmol) of the HL750-HSA stock solution synthesized in Production Example 1 to prepare a reaction solution. The resulting reaction solution was allowed to react by incubating while gently stirring overnight at 37° C. in an air atmosphere to synthesize Complex 2b. After filtering the resulting reaction product with the Amicon 10K, the reaction product was washed three times with water. Subsequently, the reaction solution was filtered with a Durapore PVDF membrane (0.45 µm) followed by diluting to 60 µL with water to prepare a Complex 2b solution. As a result of analyzing by MALDI-TOF MS, the average mass of the synthesized Complex 2b was 102.1 kDa and 10.5 molecules of N-linked sugar chain (aldehyde compound represented by formula (1b)) were bound per molecule thereof.

Example 3

HL750-HSA bound with the N-linked sugar chain represented by formula (c') (asialo-HLF-HSA, to be referred to as "Complex 2c") was synthesized.

<Synthesis of Aldehyde Compound Represented by Formula (1c)>

52 µL (0.52 µmol) of a solution of the aldehyde compound represented by formula (1), obtained by dissolving in methyl cyanide to a concentration of 10 mM in a nitrogen atmosphere, were added to a solution obtained by dissolving 1.09 mg (0.57 µmol) of an azide derivative of an N-linked sugar chain having a sugar chain represented by formula (c') (azide derivative represented by the following formula (c), GlyTech, Inc.) in 139 of DMSO. The resulting reaction solution was heated to 70° C. followed by confirming the reaction product by HPLC. After the initially added aldehyde compound was consumed, the reaction solution was cooled to room temperature to obtain a stock solution (3.8 mM) in which the aldehyde compound represented by the following formula (1c) is dissolved in DMSO. The synthesized aldehyde compound represented by formula (1c) was able to be detected by ESI-TOF MS (detected value of $C_{106}H_{147}N_{11}O_{55}$ $[M-2H]^{-2}/2$: 1226.9545, calculated value: 1226.9527).

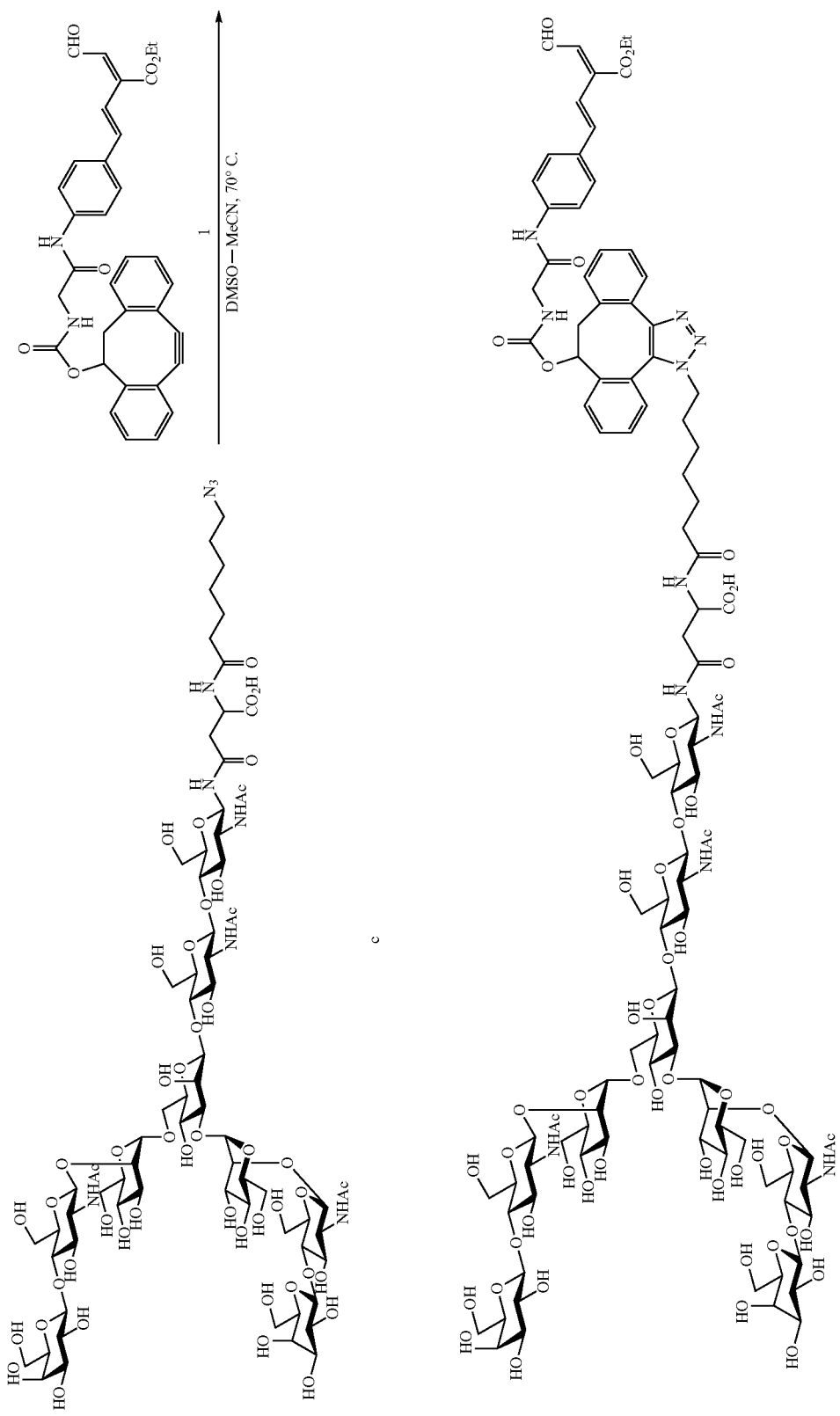

<Synthesis of Complex 2c>

30 µL (0.15 µmol) of a solution of the aldehyde compound represented by formula (1), obtained by dissolving in methyl cyanide to a concentration of 5 mM in a nitrogen atmosphere, were added to a solution obtained by dissolving 0.29 mg (0.15 µmol) of an azide derivative represented by the aforementioned formula (c) (GlyTech, Inc.) in 20 µL of DMSO. The resulting reaction solution was heated to 70° C. followed by confirming the reaction product by HPLC. After the initially added aldehyde compound was consumed, the reaction solution was cooled to room temperature followed by diluting by adding 44 µL of DMSO and 88 µL of water. Next, 88 µL (5.0 nmol) of the HL750-HSA stock solution synthesized in Production Example 1 were added followed by mixing well to prepare a reaction solution. The resulting reaction solution was allowed to react by incubating while gently stirring overnight at 37° C. in an air atmosphere to synthesize Complex 2c. After filtering the resulting reaction product with the Amicon 10K, the reaction product was washed three times with water. Subsequently, the reaction solution was filtered with a Durapore PVDF membrane (0.45 µm) followed by diluting to 100 µL with water to prepare a Complex 2c solution. As a result of analyzing by MALDI-TOF MS, the average mass of the synthesized Complex 2c was 92.6 kDa and 9.1 molecules of N-linked sugar chain (aldehyde compound represented by formula (1c)) were bound per molecule thereof.

Example 4

HL750-HSA bound with the N-linked sugar chain represented by formula (d') (GlcNAc-HLF-HSA, to be referred to as "Complex 2d") was synthesized.

<Synthesis of Aldehyde Compound represented by Formula (1d)>

30 µL (0.15 µmol) of a solution of the aldehyde compound represented by formula (1), obtained by dissolving in methyl cyanide to a concentration of 5 mM in a nitrogen atmosphere, were added to a solution obtained by dissolving 0.24 mg (0.15 µmol) of an azide derivative of an N-linked sugar chain having a sugar chain represented by formula (d') (azide derivative represented by the following formula (d), GlyTech, Inc.) in 20 µL of DMSO. The resulting reaction solution was heated to 70° C. followed by confirming the reaction product by HPLC. After the initially added aldehyde compound was consumed, the reaction solution was cooled to room temperature to synthesize the aldehyde compound represented by the following formula (1d). The synthesized aldehyde compound represented by formula (1d) was able to be detected by ESI-TOF MS (detected value of $C_{94}H_{129}N_{11}O_{45}$ $[M-2H]^{-2}/2$: 1064.9041, calculated value: 1064.8999).

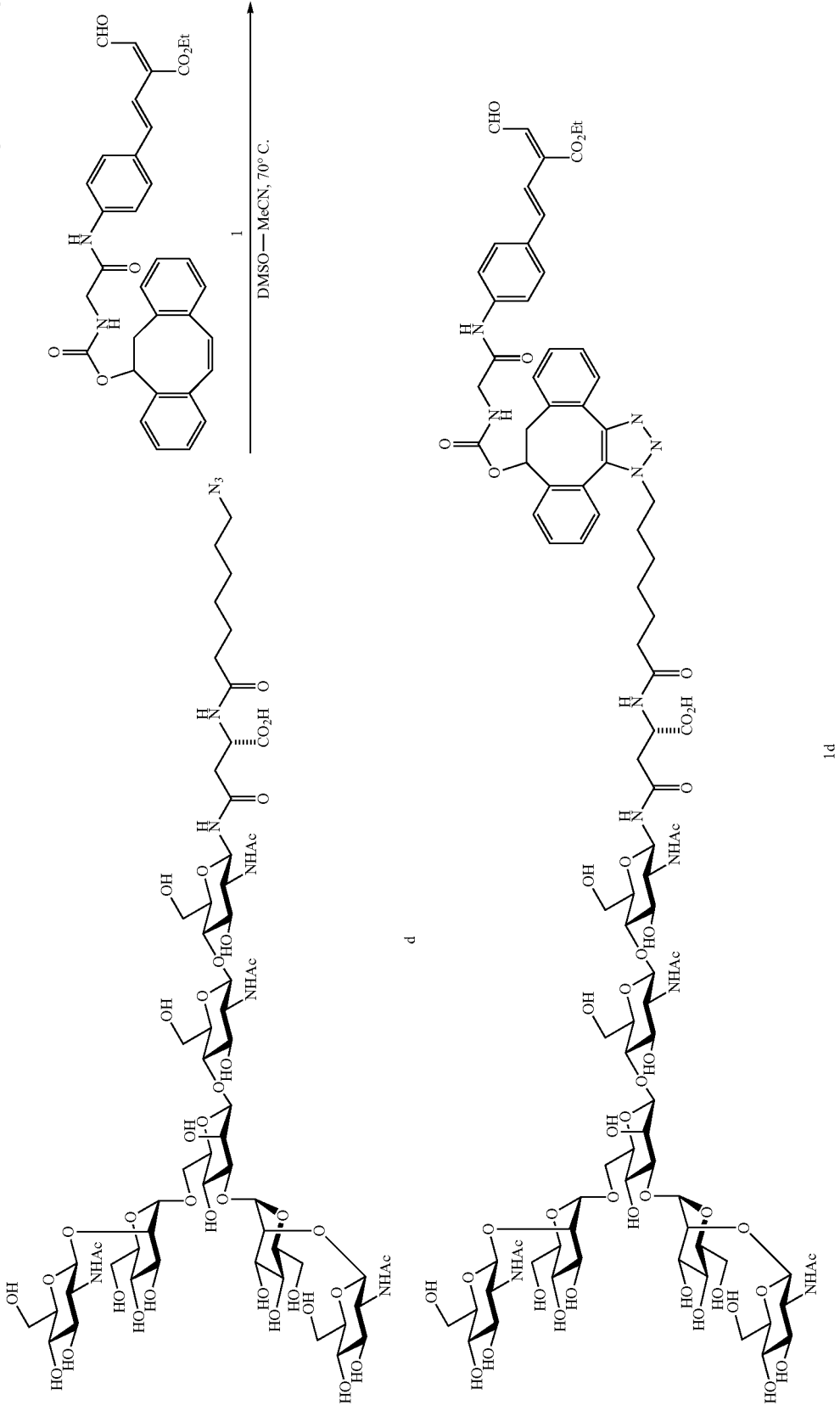

<Synthesis of Complex 2d>

Next, the reaction solution cooled to room temperature was diluted by adding 44 µL of DMSO and 88 µL of water thereto. Next, 88 µL (5.0 nmol) of the HL750-HSA stock solution synthesized in Production Example 1 were added and mixed well to prepare a reaction solution. The resulting reaction solution was allowed to react by incubating while gently stirring overnight at 37° C. in an air atmosphere to synthesize Complex 2d. After filtering the resulting reaction product with the Amicon 10K, the reaction product was washed three times with water. Subsequently, the reaction solution was filtered with a Durapore PVDF membrane (0.45 µm) followed by diluting to 100 µL with water to prepare a Complex 2d solution. As a result of analyzing by MALDI-TOF MS, the average mass of the synthesized Complex 2d was 91.9 kDa and 10.1 molecules of N-linked sugar chain (aldehyde compound represented by formula (1d)) were bound per molecule thereof.

Example 5

HL750-HSA bound with the N-linked sugar chain represented by formula (e') (Man-HLF-HSA, to be referred to as "Complex 2e") was synthesized.

<Synthesis of Aldehyde Compound represented by Formula (1e)>

30 µL (0.15 µmol) of a solution of the aldehyde compound represented by formula (1), obtained by dissolving in methyl cyanide to a concentration of 5 mM in a nitrogen atmosphere, were added to a solution obtained by dissolving 0.18 mg (0.15 µmol) of an azide derivative of an N-linked sugar chain having a sugar chain represented by formula (e') (azide derivative represented by the following formula (e), GlyTech, Inc.) in 20 µL of DMSO. The resulting reaction solution was heated to 70° C. followed by confirming the reaction product by HPLC. After the initially added aldehyde compound was consumed, the reaction solution was cooled to room temperature to synthesize the aldehyde compound represented by the following formula (1e). The synthesized aldehyde compound represented by formula (1e) was able to be detected by ESI-TOF MS (detected value of $C_{78}H_{101}N_9O_{35}$ $[M-2H]^{-2}/2$: 861.8176, calculated value: 861.8206).

[Chemical Formula 12]
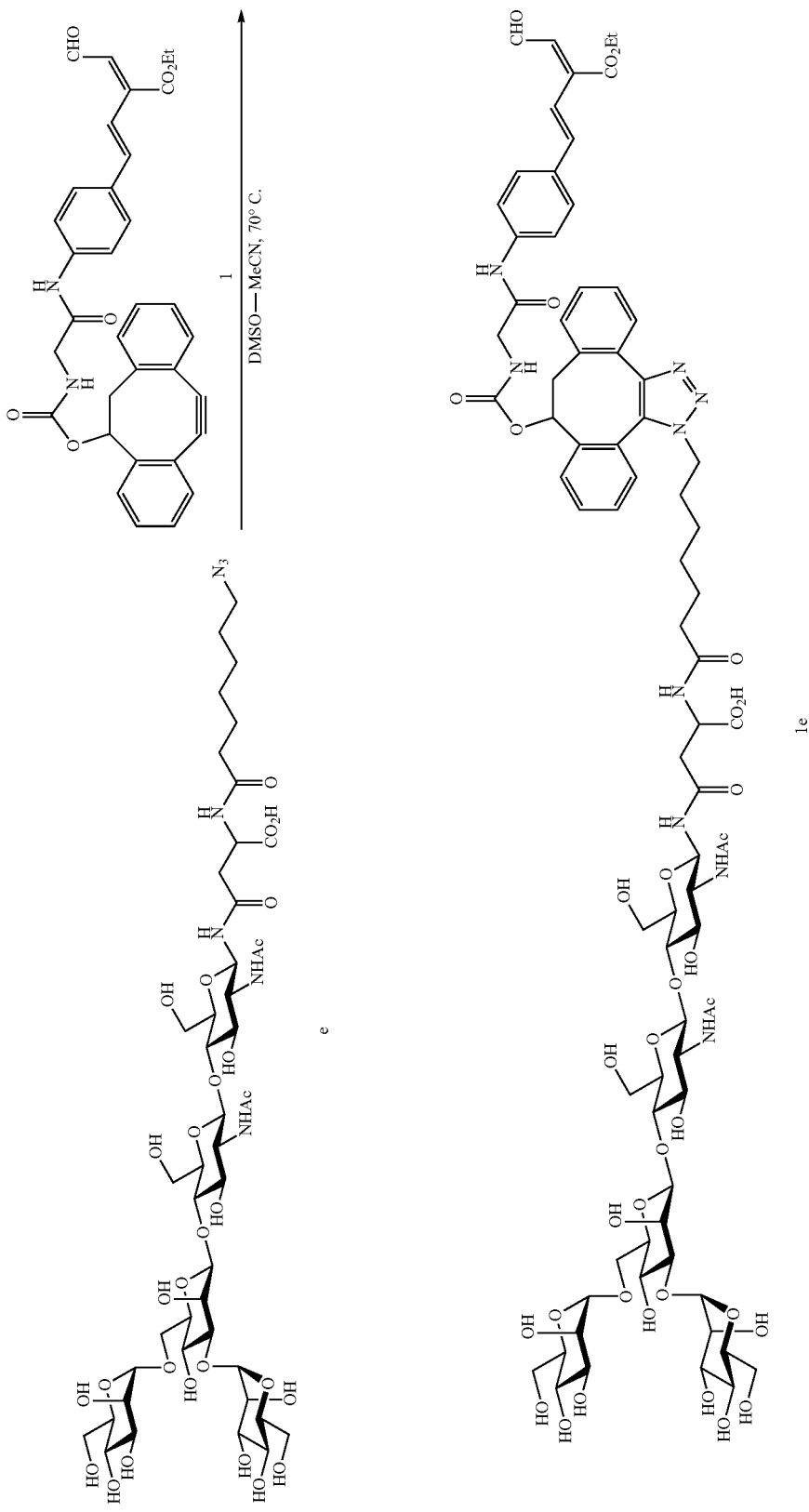

<Synthesis of Complex 2e>

Next, the reaction solution cooled to room temperature was diluted by adding 44 μL of DMSO and 88 μL of water thereto. Next, 88 μL (5.0 nmol) of the HL750-HSA stock solution synthesized in Production Example 1 were added and mixed well to prepare a reaction solution. The resulting reaction solution was allowed to react by incubating while gently stirring overnight at 37° C. in an air atmosphere to synthesize Complex 2e. After filtering the resulting reaction product with the Amicon 10K, the reaction product was washed three times with water. Subsequently, the reaction solution was filtered with a Durapore PVDF membrane (0.45 μm) followed by diluting to 100 μL with water to prepare a Complex 2e solution. As a result of analyzing by MALDI-TOF MS, the average mass of the synthesized Complex 2e was 88.5 kDa and 10.4 molecules of N-linked sugar chain (aldehyde compound represented by formula (1e)) were bound per molecule thereof.

Example 6

HL750-HSA bound with the N-linked sugar chain represented by formula (f') (Half-HLF-HSA, to be referred to as "Complex 2f") was synthesized.

<Synthesis of Aldehyde Compound represented by Formula (1f)>

30 μL (0.15 μmol) of a solution of the aldehyde compound represented by formula (1), obtained by dissolving in methyl cyanide to a concentration of 5 mM in a nitrogen atmosphere, were added to a solution obtained by dissolving 0.28 mg (0.15 μmol) of an azide derivative of an N-linked sugar chain having a sugar chain represented by formula (f') (azide derivative represented by the following formula (f), GlyTech, Inc.) in 20 μL of DMSO. The resulting reaction solution was heated to 70° C. followed by confirming the reaction product by HPLC. After the initially added aldehyde compound was consumed, the reaction solution was cooled to room temperature to synthesize the aldehyde compound represented by the following formula (1f). The synthesized aldehyde compound represented by formula (1f) was able to be detected by ESI-TOF MS (detected value of $C_{103}H_{143}N_{11}O_{53}$ $[M-2H]^{-2}/2$: 1189.9316, calculated value: 1189.9344).

[Chemical Formula 13]
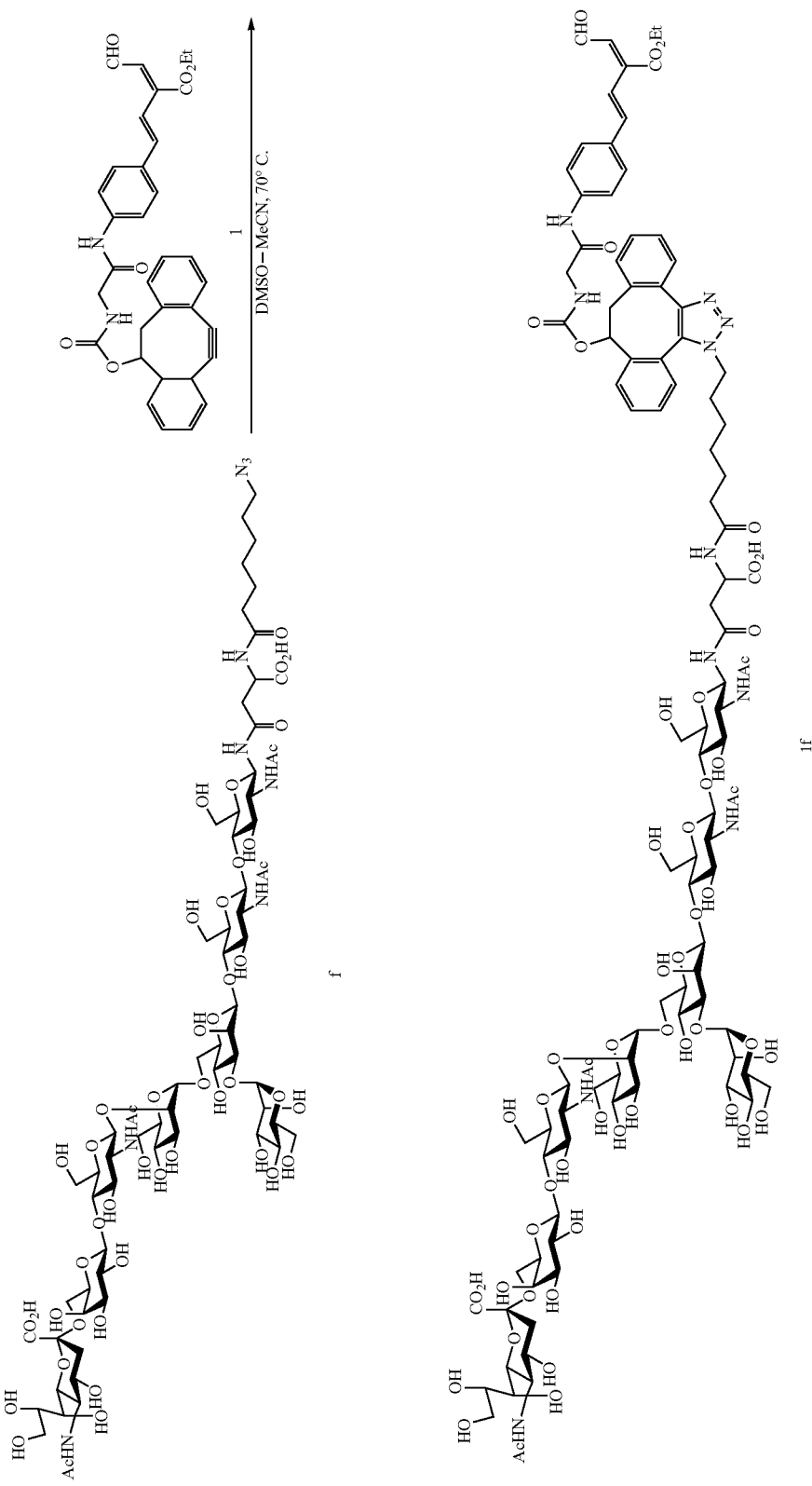

<Synthesis of Complex 2f>

Next, the reaction solution cooled to room temperature was diluted by adding 44 μL of DMSO and 88 μL of water thereto. Next, 88 μL (5.0 nmol) of the HL750-HSA stock solution synthesized in Production Example 1 were added and mixed well to prepare a reaction solution. The resulting reaction solution was allowed to react by incubating while gently stirring overnight at 37° C. in an air atmosphere to synthesize Complex 2f. After filtering the resulting reaction product with the Amicon 10K, the reaction product was washed three times with water. Subsequently, the reaction solution was filtered with a Durapore PVDF membrane (0.45 μm) followed by diluting to 100 μL with water to prepare a Complex 2f solution. As a result of analyzing by MALDI-TOF MS, the average mass of the synthesized Complex 2f was 94.0 kDa and 9.9 molecules of N-linked sugar chain (aldehyde compound represented by formula (1f)) were bound per molecule thereof.

Example 7

HL750-HSA bound with the N-linked sugar chain represented by formula (a') and the N-linked sugar chain represented by formula (c') (Hetero3-HSA, to be referred to as "Complex 2g") was synthesized.

46.7 μL (175 nmol, 17.5 eq) of the stock solution (3.8 mM) of the aldehyde compound represented by formula (1a) produced in Example 1 were mixed with a solution obtained by adding 175 μL of water and 88 μL of DMSO to 175 μL (10 nmol) of the HL750-HSA stock solution synthesized in Production Example 1 to prepare a reaction solution. The resulting reaction solution was allowed to react by incubating while stirring gently overnight at 37° C. in an air atmosphere to synthesize an intermediate in which the N-linked sugar chain represented by formula (a') was bound to HL750-HSA. A 0.5 μL aliquot of this reaction solution was removed, purified with the Amicon 10K and washed twice with water, and as a result of analyzing by MALDI-TOF MS, the average mass of the synthesized intermediate was 96.9 kDa and 8.3 molecules of the N-linked sugar chain represented by formula (a') (aldehyde compound represented by formula (1a)) were bound per molecule thereof.

Next, 2.0 μL (7.5 nmol, 7.5 eq) of the stock solution (3.8 mM) of the aldehyde compound represented by formula (1c) prepared in Example 3 were mixed with the remaining reaction solution (44 μL, 1.0 nmol) to prepare a reaction solution. The resulting reaction solution was allowed to react by incubating while gently stirring overnight at 37° C. in an air atmosphere to synthesize Complex 2g in which the N-linked sugar chain represented by formula (c') was bound to the aforementioned intermediate. The resulting reaction product was filtered with the Amicon 10K and washed three times with water. Subsequently, the reaction solution was filtered with a Durapore PVDF membrane (0.45 μm) followed by diluting with water to prepare a Complex 2g solution (50 μM). As a result of analyzing by MALDI-TOF MS, the average mass of the synthesized Complex 2g was 103.9 kDa and 2.6 molecules of the N-linked sugar chain represented by formula (c') (aldehyde compound represented by formula (1c)) were bound per molecule thereof. In other words, Complex 2g was a hetero-albumin-sugar chain complex in which the N-linked sugar chain represented by formula (a') and the N-linked sugar chain represented by formula (c') were bound to albumin at a ratio of about 8:2.

Example 8

HL750-HSA bound with the N-linked sugar chain represented by formula (a') and the N-linked sugar chain represented by formula (c') (Hetero2-HSA, to be referred to as "Complex 2h") was synthesized.

43.4 μL (163 nmol, 13.6 eq) of the stock solution (3.8 mM) of the aldehyde compound represented by formula (1a) produced in Example 1 were mixed with a solution obtained by adding 210 μL of water and 105 μL of DMSO to 210 μL (12 nmol) of the HL750-HSA stock solution synthesized in Production Example 1 to prepare a reaction solution. The resulting reaction solution was allowed to react by incubating while stirring gently overnight at 37° C. in an air atmosphere to synthesize an intermediate in which the N-linked sugar chain represented by formula (a') was bound to HL750-HSA. A 0.5 μL aliquot of this reaction solution was removed, purified with the Amicon 10K and washed twice with water, and as a result of analyzing by MALDI-TOF MS, the average mass of the synthesized intermediate was 87.1 kDa and 5.3 molecules of the N-linked sugar chain represented by formula (a') (aldehyde compound represented by formula (1a)) were bound per molecule thereof.

Next, 14.2 μL (52 nmol, 10.4 eq) of the stock solution (3.8 mM) of the aldehyde compound represented by formula (1c) prepared in Example 3 were mixed with 215 μL (5.0 nmol) of the remaining reaction solution to prepare a reaction solution. The resulting reaction solution was allowed to react by incubating while gently stirring overnight at 37° C. in an air atmosphere to synthesize Complex 2h in which the N-linked sugar chain represented by formula (c') was bound to the aforementioned intermediate. The resulting reaction product was filtered with the Amicon 10K and washed three times with water. Subsequently, the reaction solution was filtered with a Durapore PVDF membrane (0.45 μm) followed by diluting with water to prepare a complex 2h solution (50 μM). As a result of analyzing by MALDI-TOF MS, the average mass of the synthesized Complex 2h was 98.7 kDa and 4.7 molecules of the N-linked sugar chain represented by formula (c') (aldehyde compound represented by formula (1c)) were bound per molecule thereof. In other words, Complex 2h was a hetero-albumin-sugar chain complex in which the N-linked sugar chain represented by formula (a') and the N-linked sugar chain represented by formula (c') were bound to albumin at a ratio of about 5:5.

Example 9

HL750-HSA bound with the N-linked sugar chain represented by formula (a') and the N-linked sugar chain represented by formula (c') (Hetero1-HSA, to be referred to as "Complex 2i") was synthesized.

13.3 μL (50 nmol, 5.0 eq) of the stock solution (3.8 mM) of the aldehyde compound represented by formula (1a) produced in Example 1 were mixed with a solution obtained by adding 175 μL of water and 88 μL of DMSO to 175 μL (10 nmol) of the HL750-HSA stock solution synthesized in Production Example 1 to prepare a reaction solution. The resulting reaction solution was allowed to react by incubating while stirring gently overnight at 37° C. in an air atmosphere to synthesize an intermediate in which the N-linked sugar chain represented by formula (a') was bound to HL750-HSA. A 0.5 μL aliquot of this reaction solution was removed, purified with the Amicon 10K and washed twice with water, and as a result of analyzing by MALDI-TOF MS, the average mass of the synthesized intermediate was 78.9 kDa and 2.8 molecules of the N-linked sugar chain represented by formula (a') (aldehyde compound represented by formula (1a)) were bound per molecule thereof.

Next, 15.3 μL (50 nmol, 20.9 eq) of the stock solution (3.8 mM) of the aldehyde compound represented by formula (1c)

prepared in Example 3 were mixed with 119 μL (2.8 nmol) of the remaining reaction solution to prepare a reaction solution. The resulting reaction solution was allowed to react by incubating while gently stirring overnight at 37° C. in an air atmosphere to synthesize Complex 2i in which the N-linked sugar chain represented by formula (c') was bound to the aforementioned intermediate. The resulting reaction product was filtered with the Amicon 10K and washed three times with water. Subsequently, the reaction solution was filtered with a Durapore PVDF membrane (0.45 μm) followed by diluting with water to prepare a complex 2i solution (50 μM). As a result of analyzing by MALDI-TOF MS, the average mass of the synthesized Complex 2i was 97.2 kDa and 6.3 molecules of the N-linked sugar chain represented by formula (c') (aldehyde compound represented by formula (1c)) were bound per molecule thereof. In other words, Complex 2i was a hetero-albumin-sugar chain complex in which the N-linked sugar chain represented by formula (a') and the N-linked sugar chain represented by formula (c') were bound to albumin at a ratio of about 3:7.

Example 10

HL750-HSA bound with the N-linked sugar chain represented by formula (a') and the N-linked sugar chain represented by formula (c') (Hetero4-HSA, to be referred to as "Complex 2j") was synthesized.

43 μL (16 nmol, 16 eq) of the stock solution (3.8 mM) of the aldehyde compound represented by formula (1c) produced in Example 3 were mixed with a solution obtained by adding 175 μL of water and 88 μL of DMSO to 175 μL (10 nmol) of the HL750-HSA stock solution synthesized in Production Example 1 to prepare a reaction solution. The resulting reaction solution was allowed to react by incubating while stirring gently overnight at 37° C. in an air atmosphere to synthesize an intermediate in which the N-linked sugar chain represented by formula (c') was bound to HL750-HSA. A 0.5 μL aliquot of this reaction solution was removed, purified with the Amicon 10K and washed twice with water, and as a result of analyzing by MALDI-TOF MS, the average mass of the synthesized intermediate was 83.5 kDa and 5.2 molecules of the N-linked sugar chain represented by formula (c') (aldehyde compound represented by formula (1c)) were bound per molecule thereof.

Next, 4.3 μL (16 nmol, 8.0 eq) of the stock solution (3.8 mM) of the aldehyde compound represented by formula (1a) prepared in Example 1 were mixed with 88 μL (2.0 nmol) of the remaining reaction solution to prepare a reaction solution. The resulting reaction solution was allowed to react by incubating while gently stirring overnight at 37° C. in an air atmosphere to synthesize Complex 2j in which the N-linked sugar chain represented by formula (a') was bound to the aforementioned intermediate. The resulting reaction product was filtered with the Amicon 10K and washed three times with water. Subsequently, the reaction solution was filtered with a Durapore PVDF membrane (0.45 μm) followed by diluting with water to prepare a complex 2j solution (50 μM). As a result of analyzing by MALDI-TOF MS, the average mass of the synthesized Complex 2j was 97.6 kDa and 4.7 molecules of the N-linked sugar chain represented by formula (a') (aldehyde compound represented by formula (1a)) were bound per molecule thereof. In other words, Complex 2j was a hetero-albumin-sugar chain complex in which the N-linked sugar chain represented by formula (a') and the N-linked sugar chain represented by formula (c') were bound to albumin at a ratio of about 5:5.

Test Example 1

Pharmacokinetics in the case of having administered the albumin-sugar chain complexes produced in Examples 1 to 6 to mice was investigated non-invasively by detecting near-infrared fluorescence emitted from HL750.

<Acquisition of Bioimages>

First, 30 μL (1.5 nmol) of each of the albumin-sugar chain complex solutions or the HL750-HSA synthesized in Production Example 1 were diluted by adding 170 μL of physiological saline to prepare solutions for injection. The solutions for injection were injected into the tail vein of 8- to 12-week-old, female BALB/c nude mice (BALB/cAJcl-nu/nu mice) (n=4). After anesthetizing the mice with pentobarbital following injection, the mice were placed in an IVIS® biofluorescence imaging system (Kinetics Fluorescence Imager, Caliper Life Sciences Inc.) while leaving undisturbed followed by acquiring full-body fluorescence images of the mice individuals at 30 minute intervals until 3 hours after administration of the albumin-sugar chain complex. The acquired fluorescence images consisted of images obtained by removing background fluorescence (excitation light at a wavelength of 640 nm) from images obtained at an excitation light wavelength of 710 nm.

<Urinary Excretion Amounts>

The amounts of each albumin-sugar chain complex and HL750-HSA excreted into urine (as fluorescent intensity value (count)) were measured by semi-quantitative analysis from fluorescence intensities of the urinary bladder and surrounding tissue as determined by measuring fluorescence intensity for arbitrary regions of interest in the urinary bladder and surrounding tissue present in the acquired fluorescence images. The urinary excretion amounts shown in the drawings indicate the average values of the amount excreted into the urinary bladder per unit time from immediately after to 3 hours after administration.

<Fluorescence Intensity of Albumin-Sugar Chain Complex Accumulated in Various Tissues>

The small intestines of the mice were excised at 3 hours after administering an albumin-sugar chain complex followed by measuring fluorescence intensity of the gallbladder and small intestine and then measuring the accumulated amount of the albumin-sugar chain complex therein (as fluorescent intensity value (count)).

In addition, the liver and spleen of the mice were excised at 3 hours after administering an albumin-sugar chain complex followed by measurement of fluorescence intensity and then measuring the accumulated amount of the albumin-sugar chain complex therein (as fluorescent intensity value (count)).

<Measurement Results>

Fluorescence images of mouse individuals at 0.5 to 3 hours after administration to mice injected with HL570-HAS, Complex 2a, Complex 2b and Complex 2c are shown in FIGS. 2A to 2D, respectively. As a result, HL750-HSA, which was not introduced with a sugar chain, had diffused throughout the entire body of the mouse via blood vessels even at 3 hours after administration. In contrast, Complex 2a and Complex 2b, in which roughly 10 molecules of sugar chains having acidic sialic acid on the non-reducing terminal were introduced per molecule of albumin, were confirmed to have accumulated in the kidneys and urinary bladder and were determined to be rapidly excreted in urine. In addition, in the mouse administered Complex 2a and the mouse administered Complex 2b, fluorescence intensity of the entire mouse body decreased gradually and fluorescence intensity was hardly detected at all at 12 hours after administration (results not shown). In addition, in the case of similarly administering HL750-HSA, in which 1.8 molecules of the N-linked sugar chain represented by formula (a') were bound per molecule of albumin (2,6-few-HLF-HSA, to be referred to as "Complex 2SIa), to a mouse, HL750-HSA not introduced with a sugar chain diffused nearly throughout the entire body of the mouse via the blood vessels even at 3 hours after administration (results not shown). On the other hand, Complex 2c, in which roughly 10 molecules of an asialo sugar chain not having sialic acid on the non-reducing terminal thereof were introduced per molecule of albumin, was observed to accumulate in the intestine instead of the kidneys and urinary bladder, and was confirmed to be excreted into the intestinal tract via the liver and gallbladder.

Figures 3A, 3B, 3C:
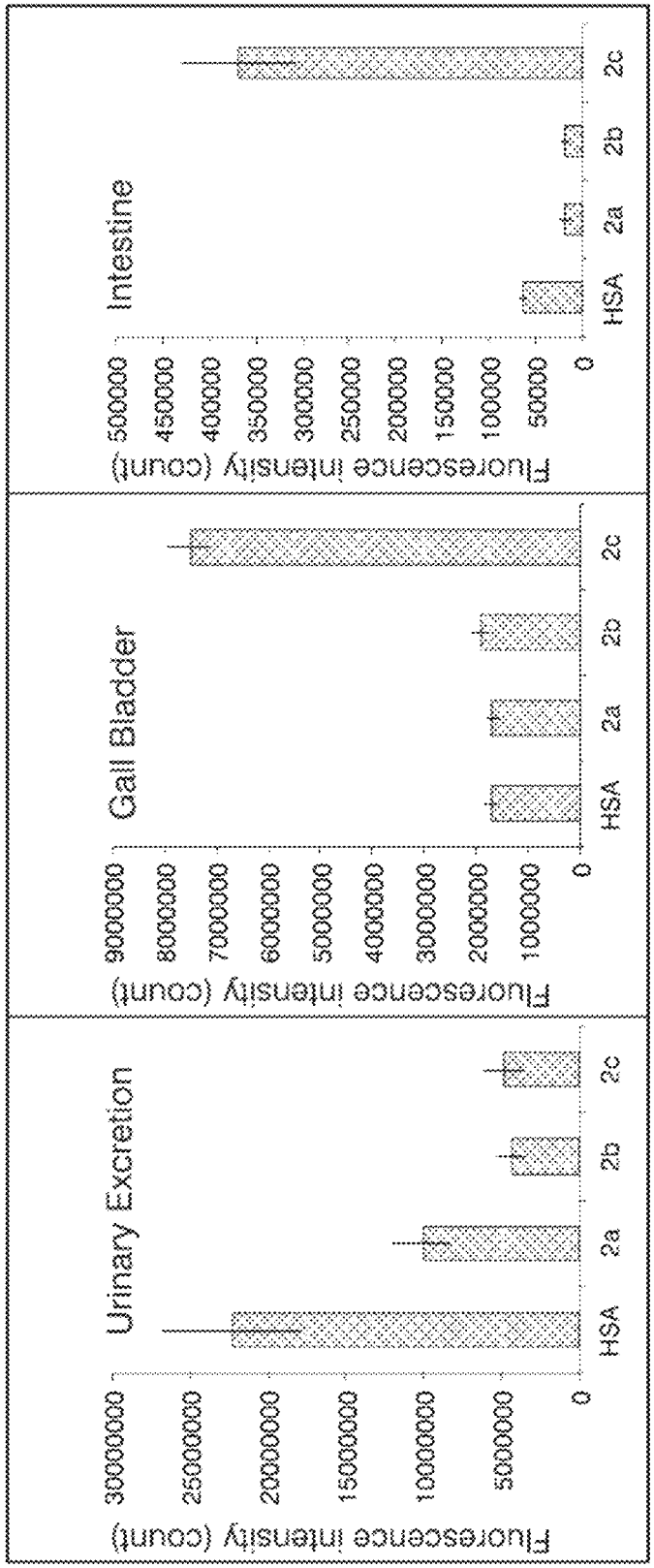
FIGS. 3A-3C respectively depict graphs showing the results of measuring the amount of albumin-sugar chain complex or HL750-HSA excreted into urine for individual mice (FIG. 3A), the results of measuring fluorescence intensity in the gallbladder at 3 hours after administration of albumin-sugar chain complex for individual mice (FIG. 3B), and the results of measuring fluorescence intensity in the small intestine at 3 hours after administration of albumin-sugar chain complex for individual mice (FIG. 3C), in a Test Example 1.

FIG. 3A indicates the results of measuring the amounts of the albumin-sugar chain complexes or HL750-HSA excreted into the urine by each mouse. As a result, the amount excreted into the kidneys and urinary bladder was highest for HL750-HSA. In addition, the urinary excreted amount was higher for Complex 2a than Complex 2b, and the rate of excretion into urine was rapid.

FIG. 3B indicates the results of measuring fluorescence intensity of the gallbladder of each mouse at 3 hours after administration, while FIG. 3C indicates the results of measuring fluorescence intensity in the small intestine of each mouse at 3 hours after administration. As a result, in the mouse administered Complex 2c, fluorescence intensity was extremely high in the gallbladder and small intestine, and Complex 2c was confirmed to bind to AGCR on the surface of hepatocytes and be excreted into the small intestine via the liver and gallbladder. In addition, Complex 2a and Complex 2b were hardly excreted into the intestinal tract at all, and were selectively excreted from the urinary bladder.

Figure 4C:
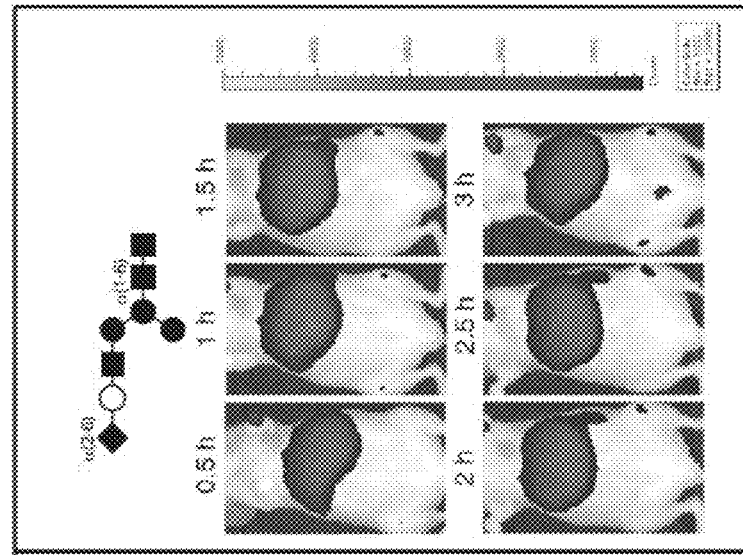
FIGS. 4A-4C respectively depict fluorescence images of mouse individuals at 0.5 hours to 3 hours after administration: mouse administered a complex 2d (FIG. 4A), mouse administered a complex 2e (FIG. 4B), and mouse administered a complex 2f (FIG. 4C), in a Test Example 1.
Figure 4B:
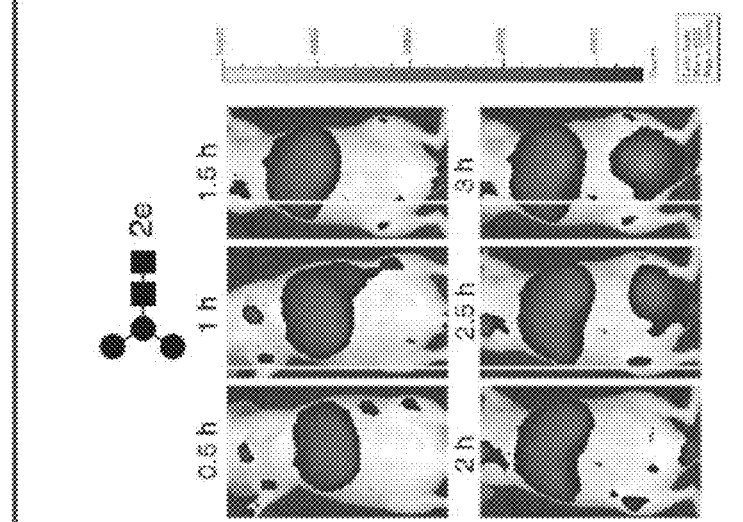
Figure 4A:
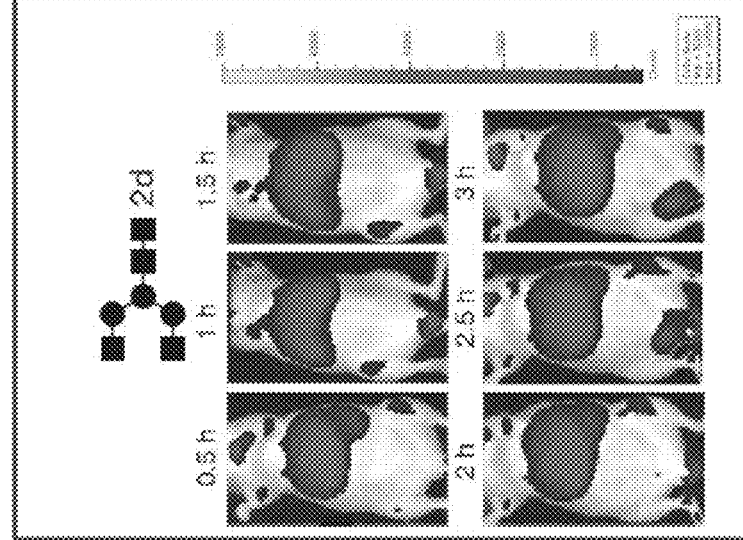

FIGS. 4A to 4C depict fluorescence images of mouse individuals at 0.5 to 3 hours after administration to mice injected with Complex 2d, Complex 2e and Complex 2f, respectively. As shown in the drawings, these complexes were confirmed to mainly accumulate in the liver and spleen.

FIG. 5A depicts fluorescence images of the liver and spleen excised from individual mice at 3 hours after administration of various complexes. In addition, FIG. 5B indicates the results of measuring fluorescence intensity in the liver of each mouse at 3 hours after administration, while FIG. 5C indicates the results of measuring fluorescence intensity in the spleen in each mouse at 3 hours after administration. As a result, in comparison with the mouse administered Complex 2a, all of the mice administered Complex 2d, Complex 2e and Complex 2f demonstrated extremely high levels of fluorescence intensity in the liver and spleen, and these albumin-sugar chain complexes were determined to selectively accumulate in the liver and spleen.

Livers excised from mice were subjected to tissue staining to investigate those portions of the liver where Complex 2d, Complex 2e and Complex 2f accumulate. More specifically, livers excised from the mice were fixed by immersing for 24 hours in 4% PFA solution at 4° C. followed by immersing for 24 hours in PBS containing 15% sucrose at 4° C. and then immersing for 24 hours in PBS containing 30% sucrose at 4° C. After freezing the fixed livers in OCT Compound® at −78° C., thin sections of the livers were prepared having a thickness of 6 μm to 8 μm. After incubating these thin sections for 30 minutes in a blocking buffer (PBST buffer containing 3% BSA, 10% goat serum and 0.1 M glycine), the thin sections were immersed in primary antibody solutions consisting of a 300-fold dilution of rat anti-Desmin antibody (product no.: RB-9014, Thermo Fisher Scientific Inc.), a 200-fold dilution of rat anti-LYVE-1 antibody (product no.: ab14917, Abcam Plc) or a 200-fold dilution of rat anti-F4/80 antibody (product no.: MCA497GA, AbD Serotec Ltd.) and incubated overnight at 4° C., followed by immersing in a secondary antibody solution consisting of a 200-fold dilution containing both Alexa Fluor 488-labeled anti-rat IgG antibody and Alexa Fluor 555-labeled anti-rat IgG antibody and incubating for 2 hours at room temperature. These thin sections were subsequently further immersed in a 2500-fold dilution of Hoechst 33258 (Dojindo Laboratories) followed by mounting on slides with mounting medium (trade name: Fluoromount®, Diagnostic Biosystems Inc.). The slides on which the thin sections were placed were observed by placing in a fluorescence microscope (trade name: BX-X710 All-in-One Fluorescence Microscope®, Keyence Corp.).

As a result, Complex 2d and Complex 2f were taken up not by liver parenchymal cells, but by non-parenchymal cells. As a result of tissue staining, anti-Desmin antibody, which specifically stains stellate cells, and anti-LYVE-1 antibody, which specifically stains sinusoidal endothelial cells, were frequently co-localized with Complex 2d, while anti-F4/80 antibody, which specifically stains Kupffer cells, was not very co-localized with Complex 2d. On the basis of these results, Complex 2d was suggested to have the potential to be specifically taken up by activated stellate cells through interaction between Desmin and Vimentin.

In addition, similar to Complex 2d, Complex 2f was also suggested to have the potential to be specifically taken up by stellate cells since it also frequently co-localizes with anti-Desmin antibody and anti-LYVE-1 antibody. On the other hand, Complex 2e frequently co-localized with anti-F4/80 antibody, and was suggested to have the potential to be specifically taken up by Kupffer cells.

In this manner, changes in the elimination mechanism of a substance in the body or the site of accumulation in the body according to the type of sugar chain on the surface of that substance cannot be analyzed using the conventional bioimaging probes, and were elucidated for the first time by using a bioimaging probe consisting of the albumin-sugar chain complex according to the present invention, which uses albumin for the protein that binds the sugar chain, and in which a plurality of sugar chains are bound per molecule of albumin.

Test Example 2

In Test Example 2, since Complex 2a is mainly excreted from the kidneys while Complex 2c is mainly excreted from the intestinal tract, effects on the sugar chain abundance ratios and elimination routes were investigated using hetero complexes having an N-linked sugar chain that composes Complex 2a (formula (1a)) and an N-linked sugar chain that composes Complex 2c (formula (1c)) at various ratios.

More specifically, after administering Complexes 2a, 2c and 2g to 2j produced in Examples 1, 3 and 7 to 9 to mice in the same manner as Test Example 1, full-body fluorescence images of the mice were acquired at 30 minute intervals until 3 hours after administration. Moreover, the urinary excretion amounts of each complex and the amounts accumulated in the gallbladder and small intestine were investigated in the same manner as Test Example 1. Furthermore, the abundance ratios (molar ratios) of the sugar chains in each complex are shown in Table 1.

TABLE 1

|  | Sugar Chain of Formula (1a) | Sugar Chain of Formula (1c) |
| --- | --- | --- |
| Complex 2a | 10 | 0 |
| Complex 2g | 8 | 2 |
| Complex 2h | 5 | 5 |
| Complex 2i | 3 | 7 |
| Complex 2c | 0 | 10 |
| Complex 2j | 5 | 5 |

FIG. 6A indicates the results of measuring the amount of albumin-sugar chain complex excreted into urine for each mouse, FIG. 6B indicates the results of measuring fluorescence intensity in the gallbladder of each mouse at 3 hours after administration, and FIG. 6C indicates the results of measuring fluorescence intensity in the small intestine of each mouse at 3 hours after administration. As a result, the elimination route of the complexes was observed to tend to shift from the kidneys to the gallbladder and small intestine as the abundance ratio of the sugar chain of formula (1c), not having sialic acid on the non-reducing terminal thereof, increased. On the basis of these results, it was determined that the elimination route of a substance in the body is affected by the type of sugar chain on the surface of that substance, and particularly whether or not the non-reducing terminal contains sialic acid, and that in the case of administering a substance into the body, the pharmacokinetics of that substance can be controlled by adjusting the sugar chains present on the surface of that substance.

Furthermore, although Complex 2h and Complex 2j both contain the sugar chain of formula (1a) and the sugar chain of formula (1c) at a ratio (molar ratio) of 1:1, Complex 2h is easily excreted from the kidneys while Complex 2j is easily excreted into the small intestine, thus demonstrating a difference between the two. Since the order in which albumin was glycosylated differs between the two, which sugar chain is linked to a lysine residue on the surface of an albumin molecule was suggested to be important.

Test Example 3

α(2-3) sialoprotein is specifically taken up by cancer cells through interaction with selectin.

Therefore, pharmacokinetics in the body were observed by administering Complex 2b produced in Example 2 to a cancer model mouse transplanted with cultured carcinoma cell line A431 cells.

$3\times10^6$ A431 cells were transplanted near the right shoulder of an 8-week-old, female BALB/c nude mouse followed by allowing two weeks to elapse to obtain a cancer model. After administering the A431 cells to the cancer model mouse in the same manner as Test Example 1, full-body fluorescence images of the mouse were acquired at 30 minute intervals until 5 hours after administration.

Figure 7:
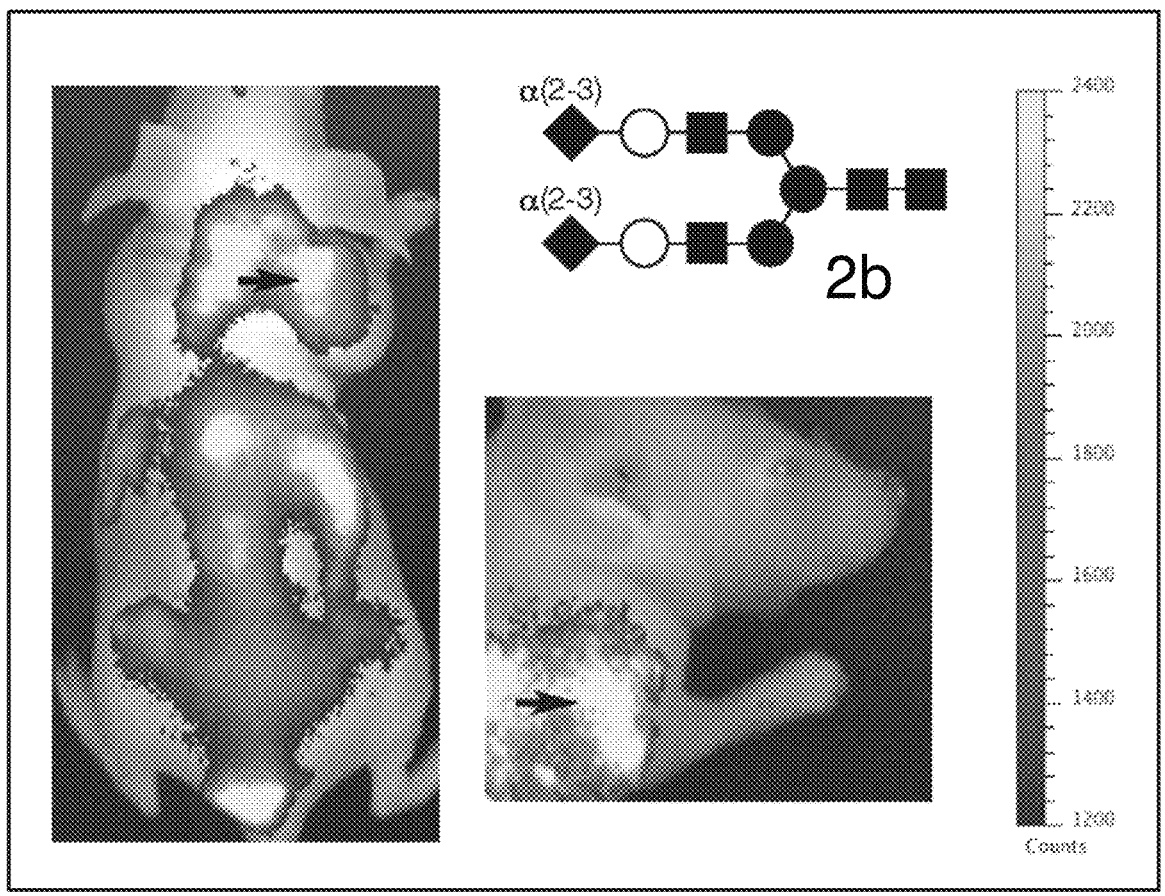
FIG. 7 depicts fluorescence images of a mouse individual at 1 hour after administration of a complex 2b in a Test Example 3.

FIG. 7 depicts fluorescence images of a mouse individual at 1 hour after injecting Complex 2b. The areas indicated by arrows in the photographs indicate the location where the A431 cells were transplanted. Complex 2b was rapidly taken up by the A431 cells 1 hour after administration. In addition, nearly all of Complex 2b was excreted at 5 hours after administration (not shown).

The invention claimed is:

1. An albumin-sugar chain complex comprising five or more molecules of an asparagine-linked sugar chain bound per molecule of albumin, the asparagine-linked sugar chain having a structure represented by the general formula (I) below:

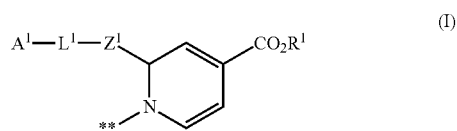

where $A^1$ is a group in which an N-linked sugar chain is bound to an amide nitrogen atom of a side chain of an Asn residue, $L^1$ is a linking group which is bound to the Asn residue at a nitrogen atom not bound to the sugar chain, $Z^1$ is a 1,2-phenylene group, a 1,3-phenylene group, or a 1,4-phenylenen group, $R^1$ is an alkyl group having 1 to 6 carbon atoms, and ** is a site that is bound to a carbon atom bound to an amino group on a side chain of a lysine residue of albumin.

2. The albumin-sugar chain complex according to claim 1, wherein the sugar on a non-reducing terminal of the asparagine-linked sugar chain comprises a sugar selected from the group consisting of N-acetylglucosamine, galactose, mannose and sialic acid.

3. The albumin-sugar chain complex according to claim 1, wherein the asparagine-linked sugar chain is one or more types of a sugar selected from the group consisting of the following formulas (a') to (f'):

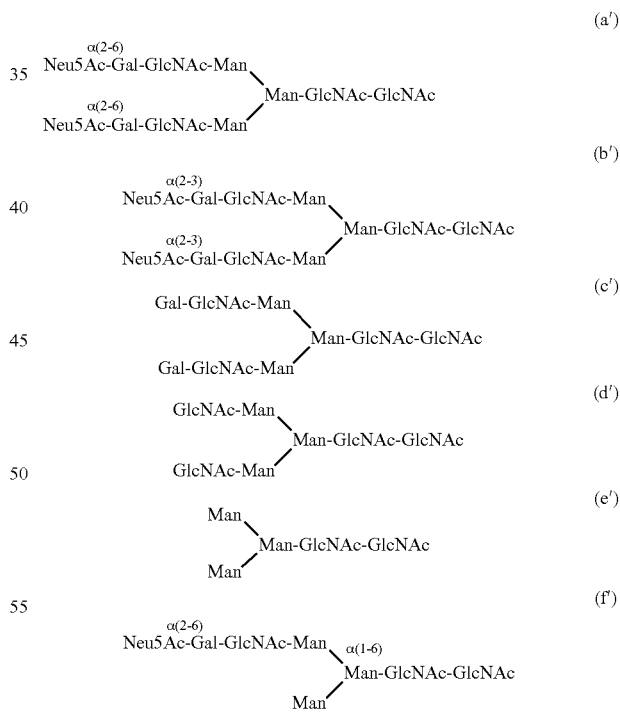

wherein, Neu5Ac represents N-acetylneuraminic acid, Gal represents galactose, GlcNAc represents N-acetylglucosamine and Man represents mannose.

4. A functional molecule carrier for selectively delivering a functional molecule to a target tissue in the body, comprising the albumin-sugar chain complex according to claim 1.

5. A functional molecule carrier for selectively delivering a functional molecule to a target tissue in the body, comprising the albumin-sugar chain complex according to claim 1, wherein the target tissue is hepatic stellate cells, and the non-reducing terminal of the asparagine-linked sugar chain is N-acetylglucosamine.

6. A functional molecule carrier for selectively delivering a functional molecule to a target tissue in the body, comprising the albumin-sugar chain complex according to claim 1, wherein the target tissue is hepatic Kupffer cells, and the asparagine-linked sugar chain is branched and has mannose and N-acetylneuraminic acid at its non-reducing terminal.

7. A functional molecule carrier for selectively delivering a functional molecule to a target tissue in the body, comprising the albumin-sugar chain complex according to claim 1, wherein the target tissue is the liver or spleen, and the non-reducing terminal of the asparagine-linked sugar chain is mannose.

8. A functional molecule carrier for selectively delivering a functional molecule to a target tissue in the body, comprising the albumin-sugar chain complex according to claim 1, wherein the target tissue is cancer cells, and the non-reducing terminal of the asparagine-linked sugar chain is $\alpha(2-3)$-linked sialic acid.

9. The functional molecule carrier according to claim 4, wherein the functional molecule is a fluorescent substance or drug.

10. A bioimaging probe comprising the albumin-sugar chain complex according to claim 1 as an active ingredient thereof that is administered into the body of an animal.

* * * * *